(12) United States Patent
Kershaw et al.

(10) Patent No.: US 7,037,406 B2
(45) Date of Patent: May 2, 2006

(54) CROSS-MACHINE DIRECTION EMBOSSING OF ABSORBENT PAPER PRODUCTS HAVING AN UNDULATORY STRUCTURE INCLUDING RIDGES EXTENDING IN THE MACHINE DIRECTION

(75) Inventors: Thomas N. Kershaw, Neenah, WI (US); Dale Gracyalny, Alpharetta, GA (US); Paul Ruthven, Neenah, WI (US); Galyn Schulz, Greenville, WI (US)

(73) Assignee: Fort James Corporation, Atlanta, GA (US)

( * ) Notice: Subject to any disclaimer, the term of this patent is extended or adjusted under 35 U.S.C. 154(b) by 192 days.

(21) Appl. No.: 10/635,663

(22) Filed: Aug. 6, 2003

(65) Prior Publication Data

US 2004/0055694 A1    Mar. 25, 2004

Related U.S. Application Data

(63) Continuation-in-part of application No. 10/235,197, filed on Sep. 5, 2002, now abandoned, which is a continuation of application No. 09/709,185, filed on Nov. 9, 2000, now Pat. No. 6,455,129, which is a continuation-in-part of application No. 10/036,770, filed on Dec. 21, 2001, now Pat. No. 6,733,626.

(60) Provisional application No. 60/165,080, filed on Nov. 12, 1999.

(51) Int. Cl.
*B31F 1/07*      (2006.01)
*B31F 1/14*      (2006.01)

(52) U.S. Cl. ...................... 162/113; 162/114; 162/117; 162/205

(58) Field of Classification Search ........ 162/109–117, 162/123, 132, 204–206, 361, 362, 286; 428/153, 428/154, 156, 182–186; 156/199, 205, 209; 101/3.1, 5, 18, 23, 32; 492/20, 30, 31; 493/58; 264/280–287, 290.2
See application file for complete search history.

(56) References Cited

U.S. PATENT DOCUMENTS

| | | | | |
|---|---|---|---|---|
| 1,384,515 | A | * 7/1921 | Conradson et al. | 162/114 |
| RE27,453 | E | * 8/1972 | Schutte et al. | 162/117 |
| 3,925,127 | A | * 12/1975 | Yoshioka | 428/101 |
| 3,940,529 | A | * 2/1976 | Hepford et al. | 428/178 |
| 3,953,638 | A | * 4/1976 | Kemp | 428/154 |
| 4,469,735 | A | * 9/1984 | Trokhan | 428/154 |
| 4,803,032 | A | 2/1989 | Schulz | 264/284 |

(Continued)

FOREIGN PATENT DOCUMENTS

EP    0 806 520 A    11/1997

(Continued)

*Primary Examiner*—Eric Hug
(74) *Attorney, Agent, or Firm*—Michael W. Ferrell

(57) ABSTRACT

A method of embossing an absorbent web with a machine direction undulatory structure is described. The web has a plurality of ridges extending in its machine direction occurring at a frequency, F, across the web and the method includes providing the web to an embossing station where the web is embossed between a first and second embossing roll, each of which rolls may be provided with a plurality of embossing elements configured to define a plurality of embossing nips. At least a portion of the embossing nips are substantially oriented in a cross-machine direction with respect to the web and have a cross direction length, L. The product F×L is from about 0.1 to about 5.

57 Claims, 22 Drawing Sheets

U.S. PATENT DOCUMENTS

| | | | |
|---|---|---|---|
| 5,093,068 A | 3/1992 | Schulz | 264/284 |
| 5,328,565 A | 7/1994 | Rasch et al. | 162/113 |
| 5,656,134 A | 8/1997 | Marinack et al. | 162/281 |
| 5,885,415 A | 3/1999 | Marinack et al. | 162/111 |
| 2003/0106657 A1* | 6/2003 | Baggot | 162/123 |
| 2004/0163783 A1* | 8/2004 | Muller | 162/132 |
| 2004/0200590 A1* | 10/2004 | Wilhelm | 162/118 |

FOREIGN PATENT DOCUMENTS

| | | |
|---|---|---|
| WO | WO96/18771 | 6/1996 |

* cited by examiner

7° WALL ANGLE CENTERED ALIGNMENT

9° WALL ANGLE CENTERED ALIGNMENT

11° WALL ANGLE CENTERED ALIGNMENT

7° WALL ANGLE CENTERED ALIGNMENT

9° WALL ANGLE CENTERED ALIGNMENT

11° WALL ANGLE CENTERED ALIGNMENT

7° WALL ANGLE CENTERED ALIGNMENT

9° WALL ANGLE CENTERED ALIGNMENT

11° WALL ANGLE CENTERED ALIGNMENT

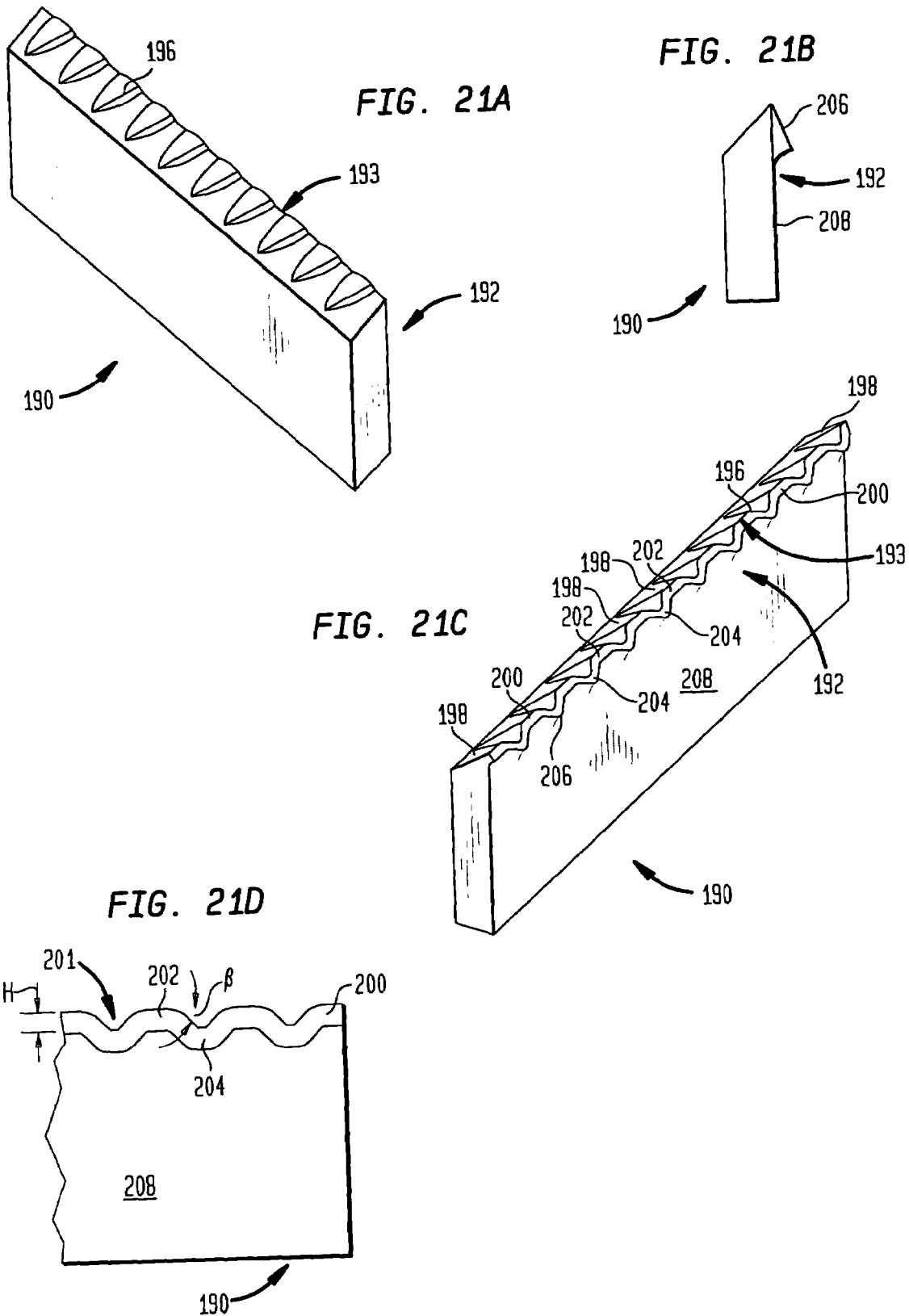

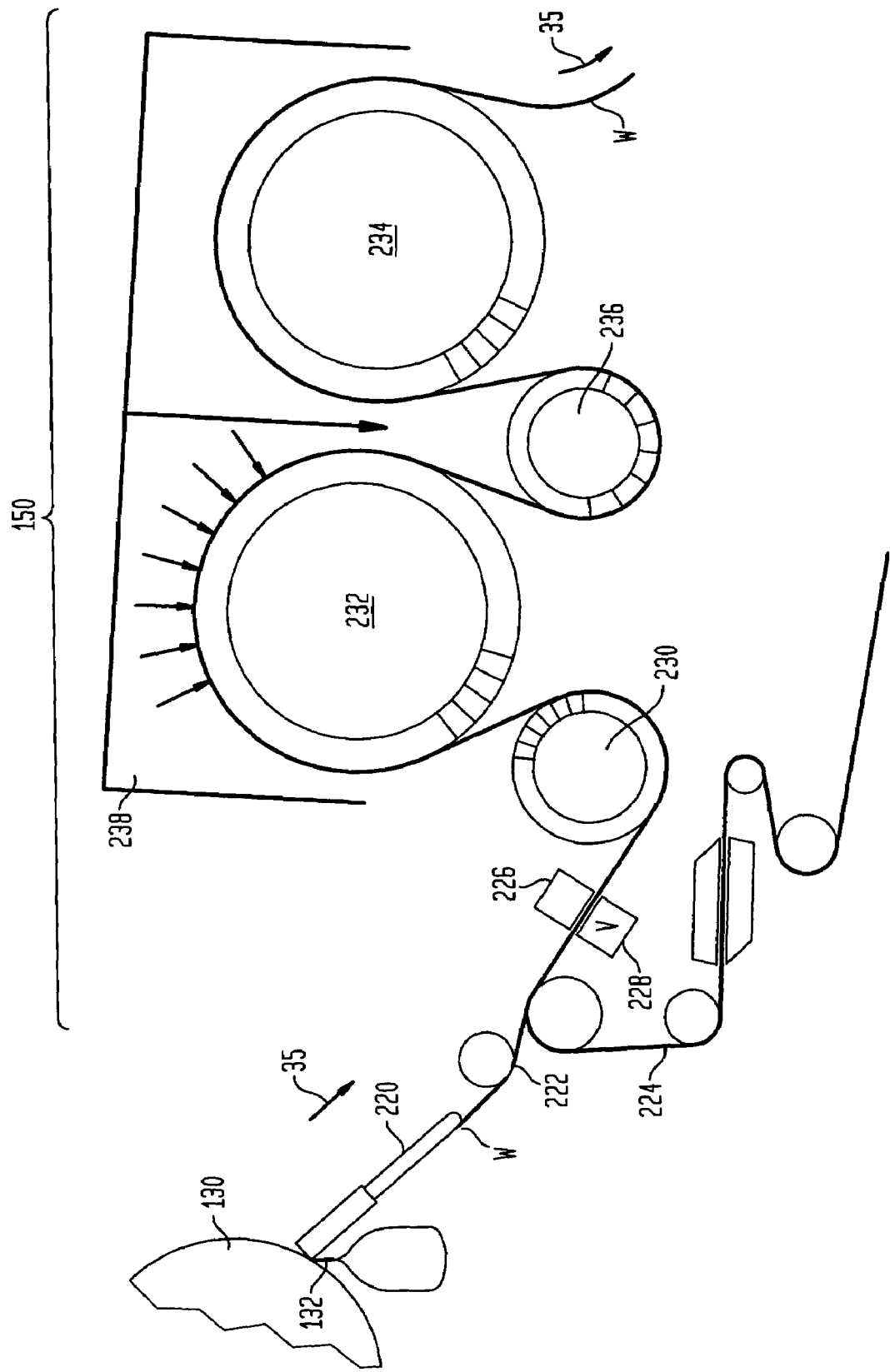

CROSS-MACHINE DIRECTION EMBOSSING OF ABSORBENT PAPER PRODUCTS HAVING AN UNDULATORY STRUCTURE INCLUDING RIDGES EXTENDING IN THE MACHINE DIRECTION

CROSS-REFERENCE TO RELATED APPLICATIONS

This application is a continuation-in-part of U.S. patent application Ser. No. 10/235,197, entitled "Single-ply Embossed Absorbent Paper Products" filed Sep. 5, 2002, now abandoned, which was a continuation application of U.S. patent application Ser. No. 09/709,185 entitled "Single-ply Embossed Absorbent Paper Products", filed Nov. 9, 2000, now U.S. Pat. No. 6,455,129, which was based upon U.S. Provisional Patent Application No. 60/165,080, of the same title, filed Nov. 12, 1999. This application is also a continuation-in-part of U.S. patent application Ser. No. 10/036,770, entitled "An Apparatus and Method for Degrading a Web in the Machine Direction While Preserving Cross-machine Direction Strength", filed Dec. 21, 2001, now U.S. Pat. No. 6,733,626. The priorities of the foregoing applications are hereby claimed.

BACKGROUND OF THE INVENTION

Embossing is carried out by passing a web between two or more embossing rolls, at least one of which carries the desired emboss pattern. Known embossing configurations include rigid-to-resilient embossing and rigid-to-rigid embossing. In a rigid-to-resilient embossing system, a single or multi-ply substrate is passed through a nip formed between a roll whose substantially rigid surface contains the embossing pattern as a multiplicity of protuberances and/or depressions arranged in an aesthetically-pleasing manner, and a second roll, whose substantially resilient surface can be either smooth or also contain a multiplicity of protuberances and/or depressions which cooperate with the rigid surfaced patterned roll. Commonly, rigid rolls are formed with a steel body which is either directly engraved upon or which can contain a hard rubber-covered, or other suitable polymer, surface (directly coated or sleeved) upon which the embossing pattern is formed by any convenient method such as, for example, being laser engraved. The resilient roll may consist of a steel core provided with a resilient surface, such as being directly covered or sleeved with a resilient material such as rubber, or other suitable polymer. The rubber coating may be either smooth or engraved with a pattern. The pattern on the resilient roll may be either a mated or a non-mated pattern with respect to the pattern carried on the rigid roll.

In a rigid-to-rigid embossing process, a single-ply or multi-ply substrate is passed through a nip formed between two substantially rigid rolls. The surfaces of both rolls contain the pattern to be embossed as a multiplicity of protuberances and/or depressions arranged into an aesthetically-pleasing manner where the protuberances and/or depressions in the second roll cooperate with those patterned in the first rigid roll. The first rigid roll may be formed, for example, with a steel body which is either directly engraved upon or which can contain a hard rubber-covered, or other suitable polymer, surface (directly coated or sleeved) upon which the embossing pattern is engraved by any conventional method, such as by laser engraving. The second rigid roll can be formed with a steel body or can contain a hard rubber covered, or other suitable polymer, surface (directly coated or sleeved) upon which any convenient pattern, such as a matching or mated pattern, is conventionally engraved or laser-engraved. In perforate embossing, a rigid-to-rigid embossing system is typically used. However, a rigid-resilient configuration can also be used for perforate embossing. In a related operation, normally referred to as "Dry Marking", the pattern is formed by protrusions on one roll which compress the sheet against an anvil roll which is normally smooth surfaced.

In perforate embossing the embossing elements are configured such that at least a portion of the web located between the embossing elements is perforated. As used herein, generally the terminology "perforated", "perforate" and the like refers to the existence of either (1) a macro-scale through aperture in the web or (2) when a macro-scale through aperture does not exist, at least incipient tearing such as would increase the transmittivity of light through a small region of the web or would decrease the machine direction strength of a web by at least 15% for a given range of embossing depths. When the degree of incipient tearing is controlled such that the loss of MD strength is less than about 15% but increased transmittivity is obtained, we prefer that the loss of MD strength is at least about 10%. In many cases, it will be advantageous to perf-emboss heavily such that the MD tensile strength is decreased about 35% to about 65%.

Commonly absorbent products such as tissue or towel are subjected to various combinations of both calendering and embossing to bring the softness and bulk parameters into acceptable ranges for premium quality products. Calendering adversely affects bulk and may raise tensile modulus, which is inversely related to tissue softness. Embossing increases product caliper (bulk) and can reduce modulus, but lowers strength and can have a deleterious effect on surface softness. Accordingly, it can be appreciated that these processes can have both beneficial and adverse effects on strength, appearance, surface smoothness and particularly thickness perception since there is a fundamental conflict between bulk and calendering.

Cross-machine direction (CD) tensile strength and stretch can be associated with consumer preference for absorbent paper products such as paper toweling. In particular, consumers prefer a strong, yet balanced, towel of which cross-machine direction (CD) strength and stretch and machine direction strength and stretch are components. Because un-embossed basesheet is typically much stronger and has more stretch in the machine direction than the cross-machine direction, an embossing process which does not lead to excessive losses in cross-machine direction tensile strength or stretch is desirable for absorbent sheet and more particularly for sheet which has machine direction ridges as described herein.

In some through air (TAD) processes, an overall pattern is imparted to the web during the forming and drying process by use of a patterned fabric having designs to enhance appearance, cross direction stretch and to balance properties. Such features may include ridges extending in the machine direction. Through air dried tissues can be deficient in surface smoothness and softness unless strategies such as calendering, embossing, chemical softeners and stratification of low coarseness fibers on the tissue's outer layers are typically employed in addition to creping.

In U.S. Pat. Nos. 5,656,134; 5,690,788; 5,685,954; 6,096,168; and 5,885,415 to Marinack et al. (hereinafter the Marinack et al. patents), the disclosure of which is incorporated by reference it was shown that paper products having highly desirable bulk, appearance (including reflectivity) and softness characteristics, can be produced by a process similar to conventional wet-press (CWP) processes by replacing the conventional creping blade with an undulatory creping blade having a multiplicity of serrated creping sections presenting differentiated creping and rake angles to the sheet. Further, in addition to imparting desirable initial characteristics directly to the sheet, the process of the Marinack et al. patents produces a sheet which is more capable of withstanding calendering without excessive degradation than a conventional wet pressed tissue web.

The process and apparatus of the Marinack et al. patents makes it possible to achieve surprisingly high absorbency in a relatively non-bulky towel thus providing an important new benefit. Similarly, webs made by way of undulatory creping can be calendered more heavily than many conventional webs while still retaining bulk and absorbency, making it possible to provide smoother, and thereby softer feeling surfaces without unduly increasing tensile modulus or unduly degrading bulk. On the other hand, if the primary goal is to save on the cost of raw materials, the tissue of the Marinack et al. patents can have surprising bulk at a low basis weight without an excessive sacrifice in strength or at low percent crepe while maintaining high caliper. Creping in accordance with the Marinack et al. patents creates a machine direction oriented shaped sheet which has higher than normal stretch in directions other than the machine direction, that is, particularly high cross-direction stretch. Embossing without the desired protocol can negate the gains realized by using the undulatory creping process and/or the benefits of molded-in machine direction ridges in the web. There is provided in accordance with the present invention creping protocols and products which enhance properties while preserving the benefits imparted to the web during its manufacture by incorporating ridges extending in the machine direction.

SUMMARY OF THE INVENTION

A method of embossing an absorbent web with an undulatory structure having a plurality of ridges extending in the machine direction occurring at a frequency, F, includes providing the web to an embossing station and embossing the web at the embossing station between a first and second embossing roll, at least one of which rolls is provided with a plurality of embossing elements and the rolls are thereby configured to define a plurality of embossing nips therebetween. At least a portion of the embossing nips defined by the embossing elements are substantially oriented in a cross-machine direction with respect to the web and have a cross direction length, L, and the product F×L is from about 0.1 to about 5. Generally, the product F×L is from about 0.2 to about 3 or from about 0.3 to about 2. In preferred cases, the product F×L is from about 0.5 to about 1.5.

Substantially all of the embossing nips may be substantially oriented in the cross-machine direction and may comprise perforate embossing nips. Typically, at least a portion of the embossing elements are male elements which are perhaps most preferably substantially oval shaped but may be substantially hexagonal shaped or substantially rectangular shaped. The cross-machine direction embossing nips are generally at an angle of from about 60° to about 120° from the machine direction, with an angle of from about 85° to about 95° from the machine direction being somewhat typical. Generally, at least a portion of the cross-machine direction embossing elements are male elements having a height of at least about 15 mils; more typically, at least a portion of the cross-machine direction embossing elements are male elements having a height of at least about 30 mils. Various alignment patterns of the elements may be employed, for instance, sometimes the cross-machine direction embossing elements are in full-step alignment, while in other cases the cross-machine direction embossing elements are in half-step alignment or in quarter-step alignment.

Generally, the cross-machine embossing element engagement is of at least about 15 mils with from about 16 to about 24 or 32 mils being somewhat typical. In preferred cases, the cross-machine direction embossing elements have angled sidewalls, wherein the sidewalls have an angle of less than about 20°.

Perhaps most preferably, the web is a creped web prepared with an undulatory creping blade, having a biaxially undulatory structure with crepe bars extending in the cross direction and ridges extending in the machine direction. In these embodiments, the web generally has from about 4 to about 50 ridges per inch extending in the machine direction with from about 8 to about 25 ridges per inch extending in the machine direction being somewhat typical. Preferably, there are from about 10 to about 16 ridges per inch extending in the machine direction. The structure includes crepe bars, that is, the web may have from about 4 to about 50 ridges per inch extending in the machine direction and from about 10 to about 150 crepe bars per inch extending in the cross-machine direction of the web.

In some preferred cases, the embossing nips oriented in the cross-machine direction comprise perforate embossing nips and the embossing step is operative to reduce the dry tensile ratio of the web and/or the wet tensile ratio of the web. So also, in general at least a portion of the embossing nips oriented in the cross-machine direction may be perforate embossing nips such that the process of embossing the web is operative to increase the transluminance ratio of the web.

In another aspect of the invention, there is provided a method of embossing an absorbent web with an undulatory structure extending in the machine direction comprising: providing a web with a plurality of ridges extending in its machine direction to an embossing station; wherein the plurality of ridges extending the machine direction of the web occur at a frequency, F, across the web; and embossing the web at the embossing station between a first and second embossing roll, at least one of which rolls is provided with a plurality of embossing elements and the rolls are thereby configured to define a plurality of embossing nips, wherein at least a portion of the embossing nips defined by the embossing elements are substantially oriented in the cross-machine direction, having a cross direction length, L, and are laterally spaced at a distance, D, with the proviso that the product F×L is between about 0.1 and about 5 or the product F×D is between about 0.1 and about 5. More preferably, F×L is between about 0.2 and 3 and F×D is between about 0.2 and 3. Still more preferably, F×L is between about 0.3 and about 2 and/or F×D is between about 0.35 and 2.5.

The inventive method may operate to reduce MD dry tensile from about 35–65% in some cases, while in others less than 15%. When MD dry tensile is reduced less than 15%, a reduction of at least about 10% is typical. It is preferred that the embossing method of the invention reduces the CD dry tensile of a basesheet by less than about 30% and even more preferably less than about 20%–25% or less than about 15% in especially preferred embodiments as seen in Table 5.

Caliper gains of 15%, 20%, 25%, 30%, 40% and more are seen with the products of the invention as compared with the unembossed basesheet from which they were made.

In still yet another aspect of the invention, there is provided an embossed absorbent web having an undulatory structure extending in the machine direction and a plurality of embossments wherein the undulatory structure of the web comprises a plurality of ridges extending in the machine direction of the web occurring at a frequency, F, across the web and at least a portion of the embossments extend substantially in the cross-machine direction. The embossments extending in the cross-machine direction extend in the cross-machine direction a distance, L'; and the embossments extending in the cross-machine direction are laterally spaced from adjacent design elements a distance, D'; with the proviso that the product F×L' is between about 0.1 and 5 or the product F×D' is between about 0.1 and 5. More preferably, F×L' is between about 0.2 and 3 and F×D' is also between about 0.2 and 3. Still more preferably, F×L' is between about 0.3 and about 2 and/or F×D' is between about 0.35 and 2.5. Preferably, the web has a dry tensile ratio of less than about 1.2 and a transluminance ratio of at least about 1.005. A transluminance ratio of at least about 1.01 is desirable in many cases.

In some preferred cases, substantially all of the embossed regions are substantially oriented in the cross-machine direction.

BRIEF DESCRIPTION OF THE INVENTION

The invention is described in detail below wherein like numerals and letters indicate like features and wherein:

FIG. 22 is a schematic diagram of a drying apparatus which may be used to dry a wet-creped web;

DETAILED DESCRIPTION

Reference will now be made in detail to preferred embodiments of the present invention, examples of which are illustrated in the accompanying drawings.

The present invention can be used to emboss a variety of types of cellulosic webs. The webs can be continuous or of a fixed length. Moreover, embossed webs can be used to produce any are recognized product, including, but not limited to, paper towels, napkins, tissue, or the like. The product can be a single ply or a multiply paper product, or a laminated paper product having multiple plies. In addition, the present invention can be used with a web made from virgin furnish, recycled furnish, or a web containing both virgin and recycled furnish, synthetic fibers, or any combination thereof.

The absorbent sheet may be a tissue product having a basis weight of from about 5 to about 25 pounds per 3,000 square foot ream, or a towel product having a basis weight of from about 10 to about 40 pounds per 3,000 square foot ream. In any case, the sheet may be prepared utilizing recycle furnish.

Figure 1:
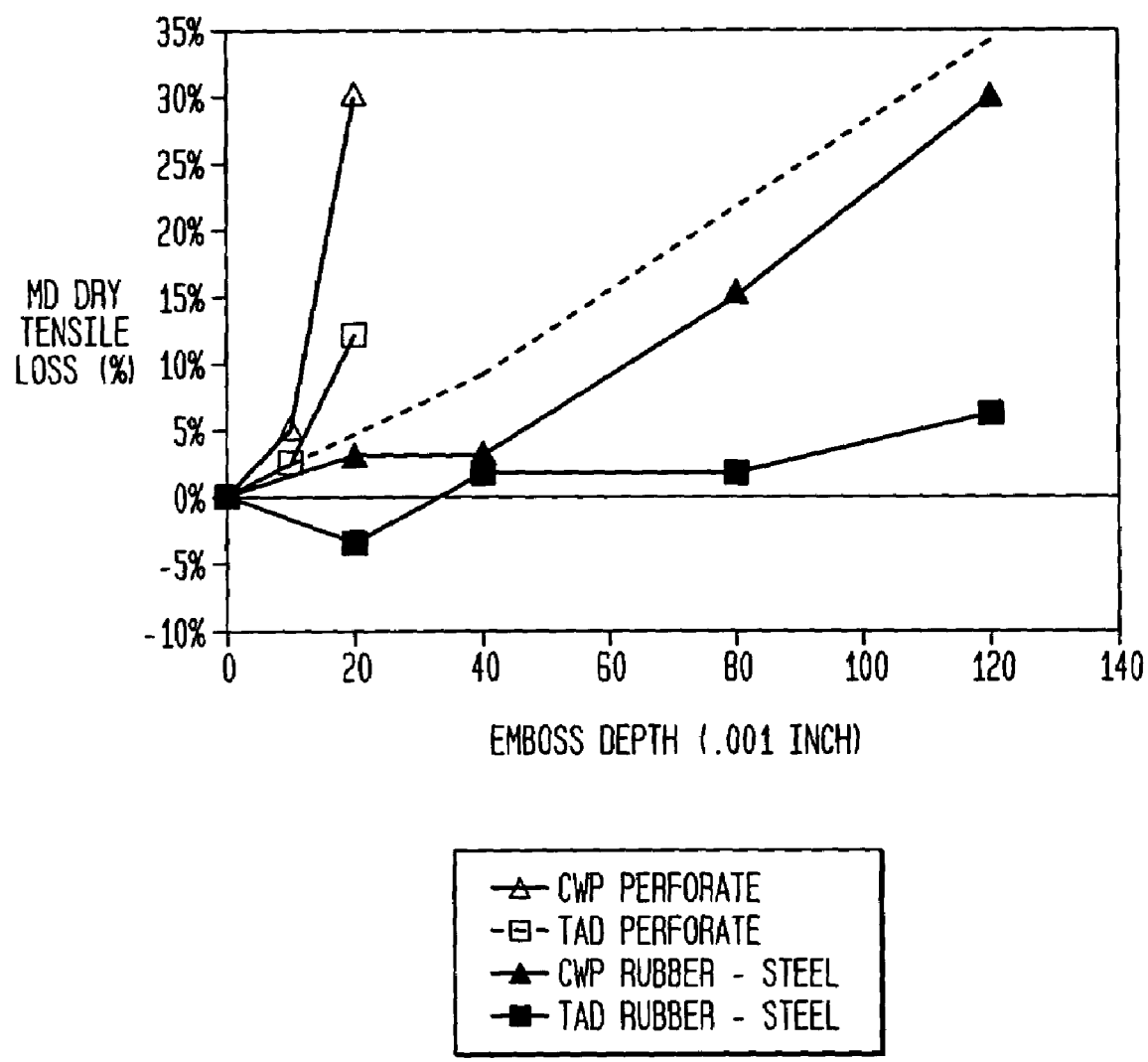
FIG. 1 is a graph of embossment depth versus MD tensile loss.

In accordance with the invention, as broadly described, the converting process includes an embossing system of at least two embossing rolls, the embossing rolls defining at least one nip through which a web to be embossed is passed. The embossing elements may be patterned to create perforations in the web as it is passed through the nip. Perforations are created when the strength of the web is locally degraded between two bypassing embossing elements resulting in either (1) a macro scale through-aperture or (2) in those cases where a macro scale through-aperture is not present, at least incipient tearing, where such tearing would increase the tansmittivity of light through a small region of the web or would decrease the machine direction strength of a web by at least 15% for a given range of embossing depths. FIG. 1 depicts a comparison of the effects on reduction of strength in the machine direction when perforate embossing a web, as defined herein, and non-perforate embossing a web. In particular, a conventional wet pressed basesheet was perforate embossed between two steel rolls. The same basesheet was non-perforate embossed in a rubber to steel configuration. In addition, a through-air-dried basesheet was also perforate and non-perforate embossed. The reduction in machine direction strength was measured for each of the sheets and the results are plotted on FIG. 1.

As shown in FIG. 1, when non-perforate embossing either a CWP or TAD web to depths of up to 40 mils, the reduction of paper strength in the machine direction is less than 5%. And, when non-perforate embossing either of the CWP or TAD webs at a depth of 80 mils, the reduction of strength of the web is less than 15%. When perforate embossing a web as disclosed in this invention, a greater reduction in strength of the web can be achieved. In the example set forth herein, strength reductions of greater than 15% are achieved when perforate embossing at depths of at least about 15 mils as compared to rubber to steel embossing which can result in these strength losses at emboss depths of over 60 mils. Accordingly, for present purposes, perforation is specifically defined as locally degrading the strength of the web between two bypassing embossing elements resulting in either (1) the formation of a macro scale through-aperture or (2) when a macro scale through-aperture is not formed, at least incipient tearing, where such tearing would either increase the transmittivity of light through a small region of the web or would decrease the machine direction strength of a web by at least the percentages set forth in FIG. 1, wherein the "at least" percentages are indicated by the dashed line.

Not being bound by theory, we believe that the superior strength reduction results achieved in some embodiments of the present invention are due to the location of the local degradation of the web when perforate embossing as compared to when non-perforate embossing. When a web is embossed, either by perforate or non-perforate methods, the portion of the web subject to the perforate or non-perforate nip is degraded. In particular, as a web passes through a non-perforate nip for embossing, the web is stressed between the two embossing surfaces such that the fiber bonds are stretched and sometimes, when the web is over embossed, which is not desired when non-perforate embossing a web, the bonds are torn or broken. When a web is passed through a perforate nip, the web fiber bonds are at least incipiently torn by the stresses caused by the two bypassing perforate elements. As stated above, however, one difference between the two methods appears to be in the location of at least incipient tearing.

Figure 2A:
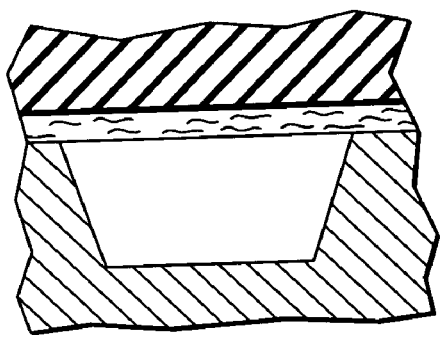
FIGS. 2A–2C illustrate the effects of over embossing a web potion in the machine direction and cross-machine direction when using rigid to resilient embossing as compared to perforate embossing a web as in FIG. 2D.
Figure 2B:
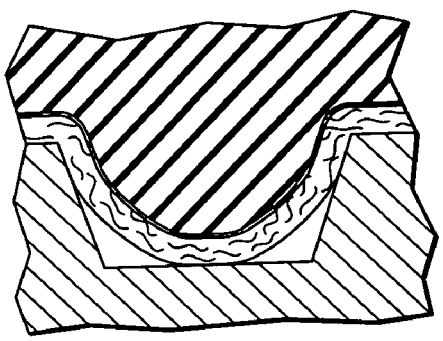
Figure 2C:
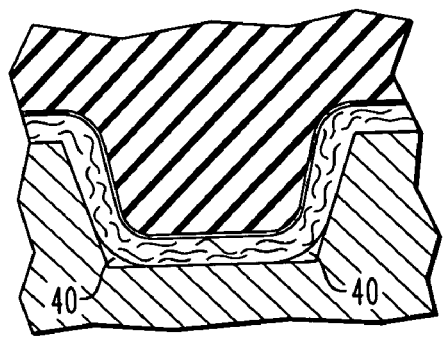

When a web is over-embossed in a rubber to steel configuration, the male steel embossing elements apply pressure to the web and the rubber roll, causing the rubber to deflect away from the pressure, while the rubber also pushes back. As the male embossing elements roll across the rubber roll during the embossing process, the male elements press the web into the rubber roll which causes tension in the web at the area of the web located at the top edges of the deflected rubber roll, i.e., at the areas at the base of the male embossing elements. When the web is over-embossed, tearing can occur at these high-tension areas. More particularly, FIGS. 2A–2C depicts rubber to steel embossing of a web at various embossing depths. FIG. 2A depicts embossing of a web at approximately 0 mils. In this configuration the rubber roll pins the web at the points where the web contacts the steel roll elements tops. Typically no tearing will occur in this configuration. In FIG. 2B, where the embossing depth is approximately the height of the steel embossing element, the web is pinned at the element tops and at a point between the bases of the adjacent steel elements. As with the configuration depicted in FIG. 2B, tearing does not typically occur in this configuration for conventional embossing procedures. FIG. 2C depicts an embossing depth comparable to or greater than the height of the steel element. In this configuration, the "free span" of the web, i.e., the sections of the web that are not pinned between the rubber and steel rolls, becomes shorter as the rubber material fills the area between the adjacent elements. When web rupturing occurs, it tends to occur near the last location where web movement is possible; that is, the area of degradation 40 is the last area that is filled by the rubber material, namely the corners where the bases of the elements meet the surface of the emboss roll.

Figure 2D:
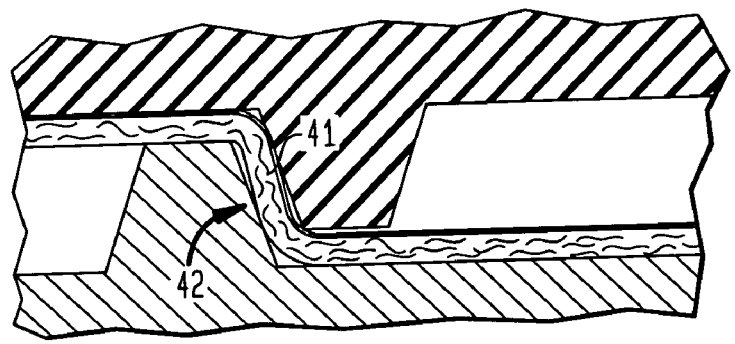

When a web is perforate embossed, on the other hand, the areas of degradation 42, as shown in FIG. 2D, are located along the sides of the perforate embossing elements in embossing nip 41. It appears that as a result of this difference the degradation of the web and the resultant reduction of web strength is dramatically different.

In one embodiment according to the present invention, the embossing rolls have substantially identical embossing element patterns, with at least a portion of the embossing elements configured such that they are capable of producing perforating nips which are capable of perforating the web. As the web is passed through the nip, an embossing pattern is imparted on the web. It is preferred that the embossing rolls be either steel or hard rubber, or other suitable polymer. The direction of travel of the web as it passes through the nip is referred to as the machine direction shown in the various Figures as MD 35. The transverse direction of the web that spans the emboss roll is referred to as the cross-machine direction and is referred to as CD 37. It is further preferred that a predominant number, i.e., at least 50% or more, of the perforations are configured to be oriented such that the major axis of the perforation is substantially oriented in the cross-machine direction. An embossing nip is substantially oriented in the cross-machine direction if the nip is at an angle of from about 60° to 120° from the machine direction of the web.

Figure 3A:
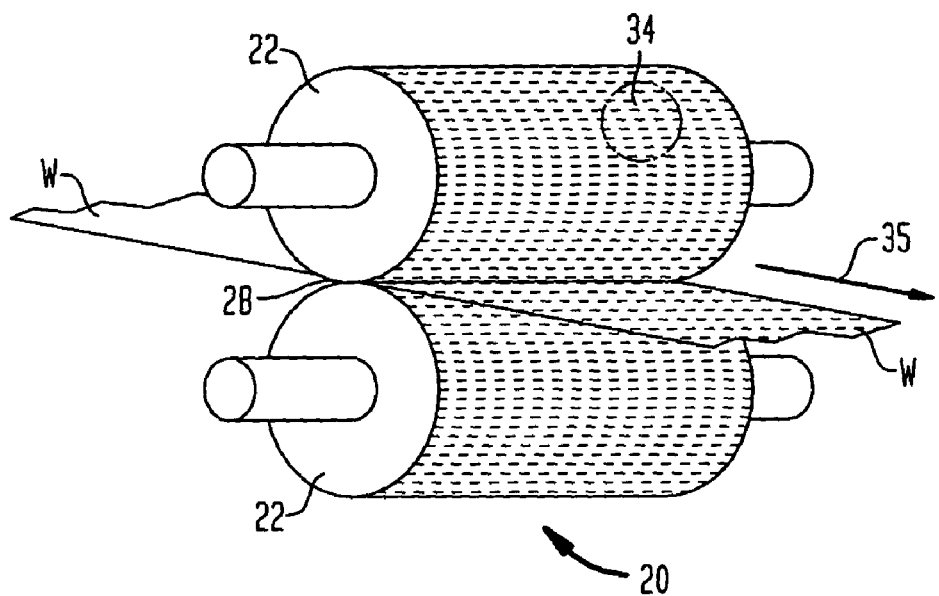
FIG. 3A is a schematic diagram illustrating embossing a web with embossing rolls having cross-direction embossing elements in accordance with the invention.
Figure 4:
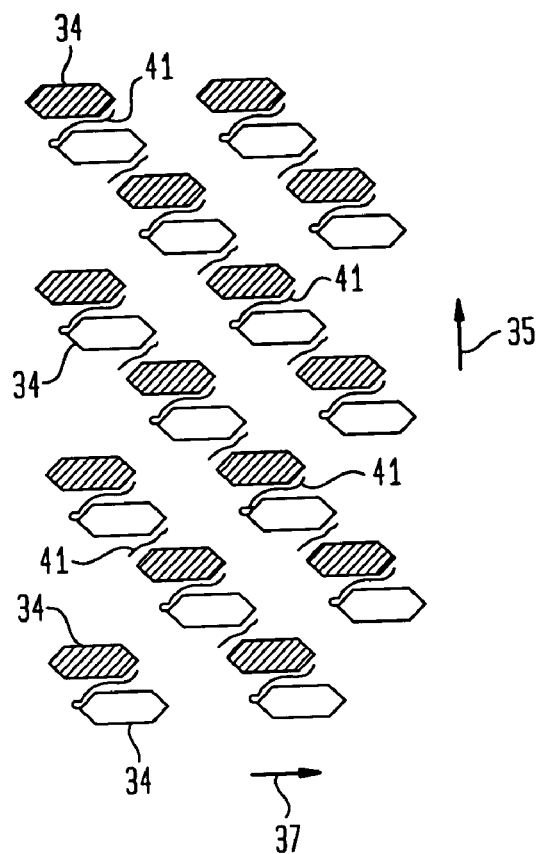
FIG. 4 illustrates cross-machine direction elements according to another embodiment of the present invention.
Figure 5:
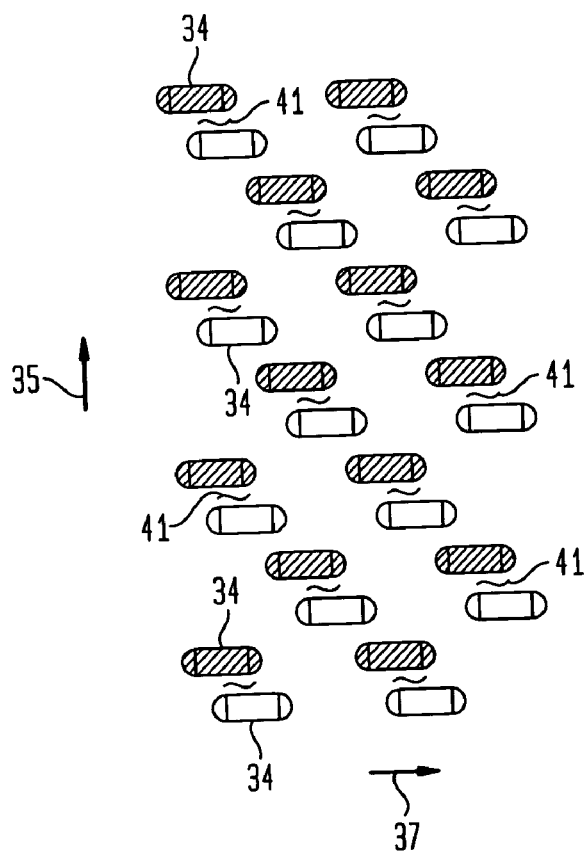
FIG. 5 illustrates cross-machine direction elements according to another embodiment of the present invention.

In an embodiment according to the present invention, and as shown in FIG. 3A, the converting process includes an embossing station 20 including embossing rolls 22 defining generally a nip 28 (which includes a plurality of nips 41 as shown in FIGS. 4 and 5) through which the web, W, to be embossed is passed. According to one embodiment, the embossing rolls 22 are matched embossing rolls. The embossing rolls can be, for example, either steel or hard rubber, or other suitable polymer. The embossing rolls 22 have at least a portion of embossing elements 34 oriented such that the major axes of the elements 34 are in the cross-machine direction 37, i.e., the elements are in the cross-machine direction. Cross direction 37 is perpendicular to or 90° offset from MD 35. It is possible to envisage configurations in which perforations extending in the cross-machine direction are formed by elements which are longer in the machine direction 35, although such a configuration would normally be sub-optimal as it would compromise the overall number of perforations which could be formed in the web. Accordingly, when we discuss elements that are configured such that the orientation of the perforation formed by those elements extends in the cross-machine direction, that should be understood to be irrespective of the shape of the portions of the element that do not contribute to the shape of the nip, whether the element be male or female. While the embossing rolls 22 can also have embossing elements oriented such that the major 20 axis of the elements is in the machine direction, a predominant number, i.e., at least 50% or more, of the elements 34 should be oriented such that they are capable of producing perforating nips extending in the cross-machine direction. In another embodiment, substantially all, i.e., at least more than 75%, of the elements 34 are oriented such that they are capable of producing perforating nips extending in the cross-machine direction. In yet another embodiment, all of the elements are oriented in the cross-machine direction. Moreover, at least about 25% of the cross-machine direction elements are perforating elements. In a preferred embodiment, all of the cross-machine direction elements are perforating elements. Thus, when the web passes through the embossing rolls 22, at least a portion of the cross-machine direction elements are aligned such that the web is perforated such that at least a portion of the perforations are substantially oriented in the cross-machine direction.

The end product characteristics of a cross-machine direction perforated embossed product can depend upon a variety of factors of the embossing elements that are imparting a pattern on the web. These factors can include one or more of the following: embossing element height, angle, shape, including sidewall angle, spacing, engagement, and alignment, as well as the physical properties of the rolls, basesheet, and other factors. Following is a discussion of a number of these factors.

An individual embossing element 34 has certain physical properties, such as height, angle, and shape, that affect the embossing pattern during an embossing process. The embossing element can be either a male embossing element or a female embossing element. The height H of an element 34 is the distance the element 34 protrudes from the surface of the embossing roll 22. It is preferred that the embossing elements 34 have a height of at least about 15 mils. In one embodiment according to the present invention, the cross-machine direction elements 34 have a height of at least about 30 mils. In another embodiment of the present invention, the cross-machine direction elements 34 have a height of greater than about 45 mils. In yet another embodiment of the invention, the cross-machine elements have a height of greater than about 60 mils. In yet another embodiment, a plurality of the elements 34 on the roll will not have planar tops but rather will have at least two regions, a first region having a first height, H, and at least a second region having a second height, H'. Preferably, the contours of the surfaces are chosen as hereinafter described with bevels and radii to avoid unintended disruptions. In a preferred embodiment, the elements 34 have a height, H, of between about 30 to 65 mils. Those of ordinary skill in the art will understand that there are a variety of element heights that can be used, depending upon a variety of factors, such as the type of web being embossed and the desired end product.

Figure 3B:
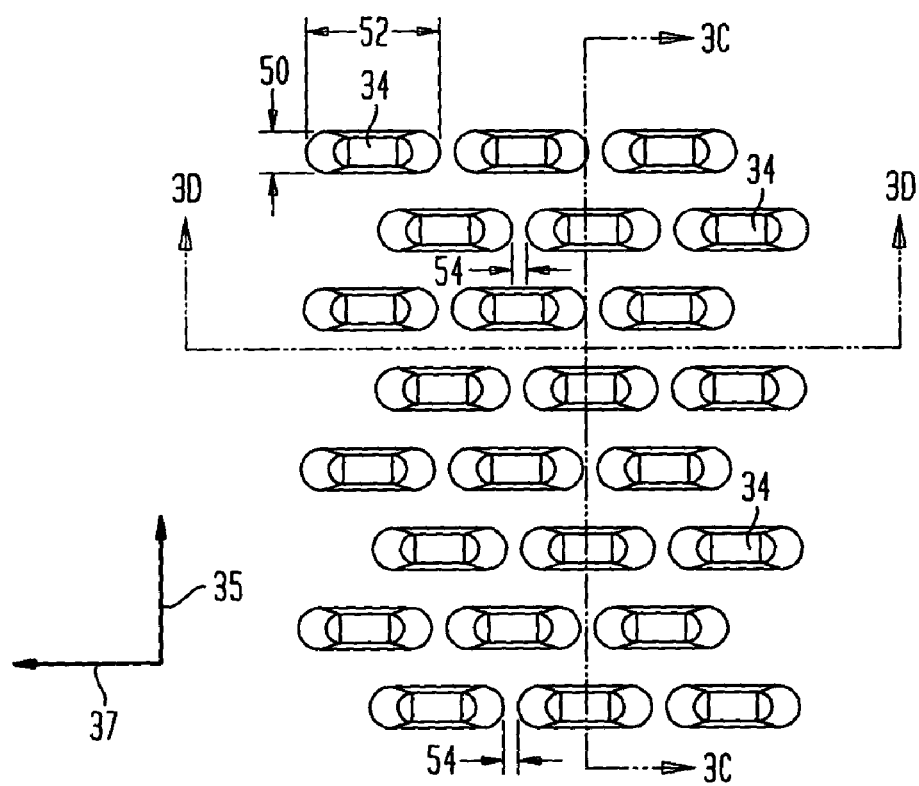
FIG. 3B is an enlarged top schematic view of an embossing roll of FIG. 3A.
Figure 3C:
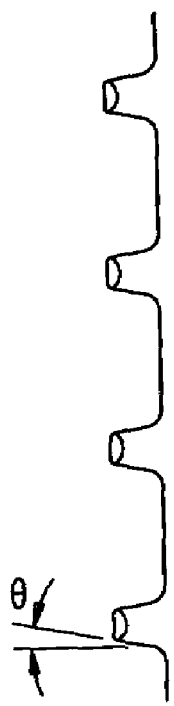
FIG. 3C is an enlarged schematic view from the cross-machine direction of an embossing roll of FIG. 3A.
Figure 3D:
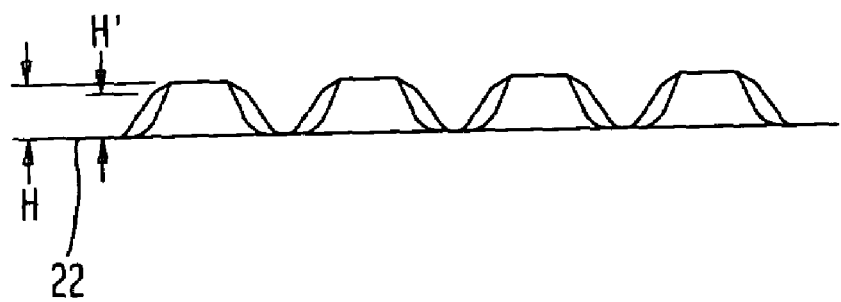
FIG. 3D is an enlarged schematic view from the machine direction of an embossing roll of FIG. 3A.

The angle of the cross-machine direction elements 34 substantially defines the direction of the degradation of the web due to cross-machine perforate embossing. When the elements 34 are oriented at an angle of about 90° from the machine direction as shown in FIG. 3B, i.e., in the absolute cross-machine direction, the perforation of the web can be substantially in the direction of about 90° from the machine direction and, thus, the degradation of the web strength is substantially in the machine direction. On the other hand, when the elements 34 are oriented at an angle from the absolute cross-machine direction, degradation of strength in the machine direction will be less and degradation of strength in the cross-machine direction will be more as compared to a system where the elements 34 are in the absolute cross-machine direction.

The angle of the elements 34 can be selected based on the desired properties of the end product. Thus, the selected angle can be any angle that results in the desired end product. In an embodiment according to the present invention, the cross-machine direction elements 34 can be oriented at an angle of at least about 60° from the machine direction of the web and less than about 120° from the machine direction of the web to define an embossing nip of like orientation. In another embodiment, the cross-machine directions element 34 are oriented at an angle from at least about 75° from the machine direction of the web and less than about 105° from the machine direction of the web. In yet another embodiment, the cross-machine direction elements 34 are oriented at an angle from at least about 80° from the machine direction of the web and less than about 100° from the machine direction of the web. In a preferred embodiment, the cross-machine direction elements 34 are oriented at an angle of about 85–95° from the machine direction. Generally speaking, the embossing elements have a cross-direction length, 52, and a machine direction width, 50. If the elements are offset from the MD and/or CD by an angle, distance 52, and 50 are respectively taken as the distance the element extends along the CD or MD, respectively. Note that the embossing elements are spaced a lateral distance, 54, as shown in FIG. 3B. Distance 54 may be, for example, 0.015 inches or so while distance 52 may be from about 50 to 150 mils when embossing a sheet with 12–16 MD ridges per inch.

A variety of element shapes can be successfully used in the present invention. The element shape is the "footprint" of the top surface of the element, as well as the side profile of the element. It is preferred that the elements 34 have a length (in the cross-machine direction/width (in the machine direction) (i.e., distance 52/distance 50) aspect ratio of at least greater than 1.0, however while noted above as suboptimal, the elements 34 can have an aspect ratio of less than 1.0. It is further preferred that an aspect ratio be about 3.5, and in many preferred cases greater than about 1.5. One element shape that can be used in this invention is a hexagonal element, as depicted in FIG. 4. Another element shape, termed an oval, is depicted in FIG. 5. For oval elements, it is preferred that the ends have radii of at least about 0.003" and less than about 0.030" for at least the side of the element forming a perforate nip 41. In one embodiment, the end radii are about 0.0135". Those of ordinary skill in the art will understand that a variety of different embossing element shapes, such as rectangular, can be employed to vary the embossing pattern. For convenience, opposed matched elements forming on embossing nip are sometimes shown as hatched. It should be appreciated that embossing nips are formed between adjacent hatched and unhatched elements in the schematic diagrams showing the embossing elements.

In one embodiment, at least a portion of the elements 34 are beveled. In particular, in one embodiment the ends of a portion of the elements 34 are beveled. Oval elements with beveled edges are depicted in FIGS. 3A–3D. By beveling the edges, the disruptions caused by the embossing elements can be better directed in the cross-machine direction, thereby reducing cross-machine direction degradation caused by the unintentional machine direction disruptions. The bevel dimensions can be from at least abut 0.010" to at least about 0.025" long in the cross-machine direction and from at least about 0.005" to at least about 0.015" in the z-direction. Other elements, such as hexagonal elements, can be beveled, as well.

The cross-machine direction sidewall of the elements 34 defines the cutting edge of the elements 34. According to one embodiment of the present invention, the cross-machine direction and machine direction sidewalls of the elements 34 are angled in as seen in FIGS. 3A–3D. As such, when the cross-machine direction sidewalls are angled, the base of the element 34 has a width, that is larger than that of the top of the element. It is preferred that the cross-machine direction sidewall angle be less than about 20°. It is further preferred that the cross-machine direction sidewall angle be less than about 17°. It is still further preferred that the cross-machine direction sidewall angle be less than about 14°. Finally, in a preferred embodiment the cross-machine direction sidewall angle is less than about 11°. It is further preferred that the cross-machine direction sidewall angle be between about 7° and 11°. The cross direction sidewall angle, θ, is measured from a perpendicular to the embossing roll surface.

When the opposing elements 34 of the embossing rolls are engaged with each other during an embossing process, the effect on the web is impacted by at least element spacing, engagement, and alignment. When perforate embossing, the elements 34 are spaced such that the clearance between the sidewalls of elements of a pair, i.e., one element 34 from each of the opposing embossing rolls 22, creates a nip 41 that perforates the web as it is passed through the embossing rolls 22. If the clearance between elements 34 on opposing rolls is too great, the desired perforation of the web may not occur. On the other hand, if the clearance between elements 34 is too little, the physical properties of the finished product may be degraded excessively or the embossing elements themselves could be damaged. The required level of engagement of the embossing rolls is at least a function of the embossing pattern (element array, sidewall angle, and element height), and the basesheet properties, e.g., basis weight, caliper, strength, and stretch. At a minimum, it is preferred that the clearances between the sidewalls of the opposing elements of the element pair be sufficient to avoid interference between the elements. In one embodiment, the minimum clearance is about a large fraction of the thickness of the basesheet. For example, if a conventional wet press (CWP) basesheet having a thickness of 4 mils is being embossed, the clearance can be at least about 2–3 mils. If the basesheet is formed by a process which results in a web with rather more bulk, such as, for example, a through air dried (TAD) method or by use of an undulatory creping blade, the clearance could desirably be relatively less. Those of ordinary skill in the art will be able to determine the desired element spacing of the present invention based on the factors discussed above using the principles and examples discussed further herein.

As noted above, in one embodiment it is preferred that the height of the elements 34 be at least about 30 mils, and it is further preferred that the height be from about 30 to 65 mils. Engagement, as used herein, is the overlap in the z-direction of the elements from opposing embossing rolls when they are engaged to form a perforating nip. The engagement overlap should be at least 1 mil.

Figure 6A:
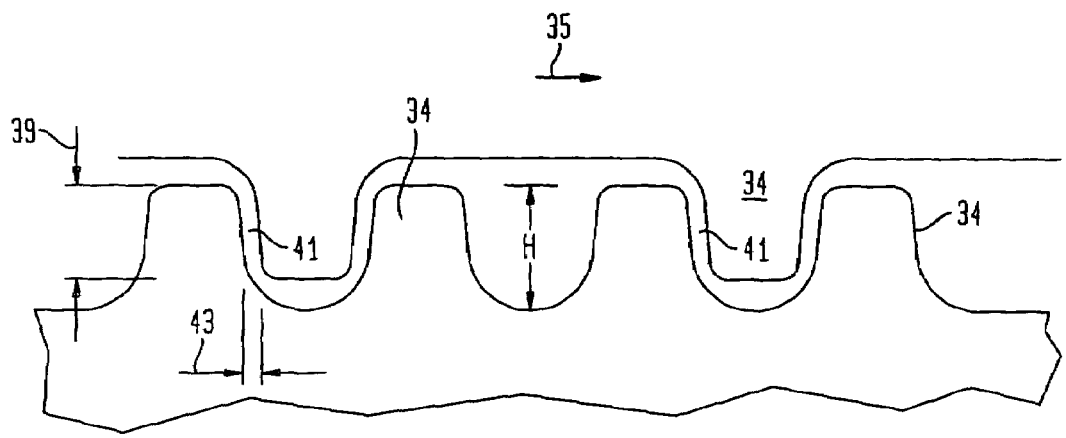
FIGS. 6A–6C are schematic side views of the cross-machine direction elements of embodiments of the present invention having differing wall angles and illustrating the effect of the differing wall angles.
Figure 6B:
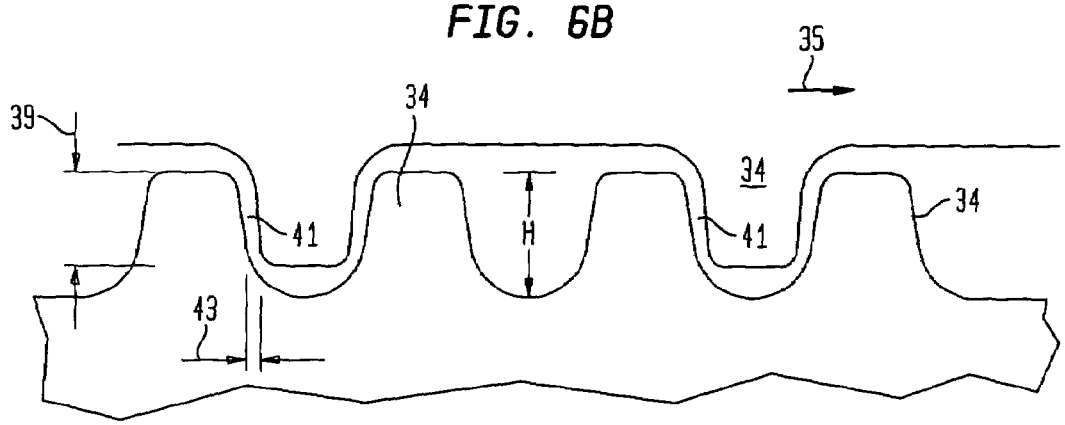
Figure 6C:
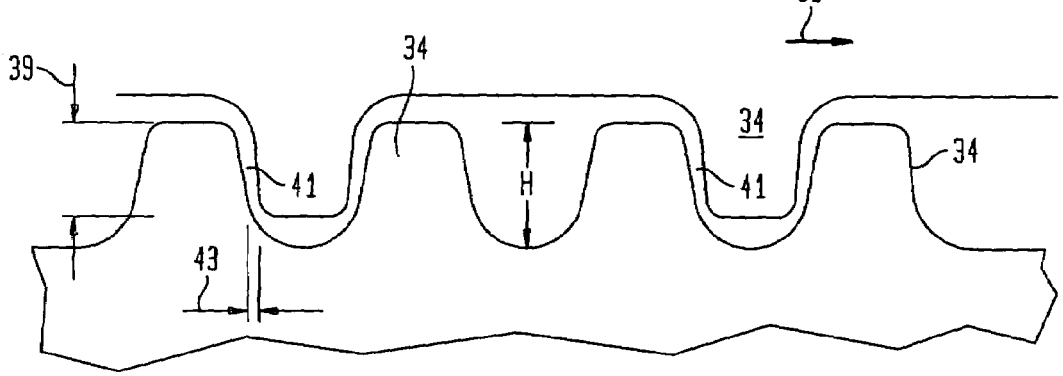

In one embodiment, the engagement 39 is at least about 15 mils. Various engagements are depicted in FIGS. 6A–8C. In particular, FIGS. 6A–6C depict a 32 mil engagement. That is, the overlap of the elements, in the z-direction, is 32 mils. The desired engagement is determined by a variety of factors, including element height, element sidewall angle, element spacing, desired effect of the embossing elements on the basesheet, and the basesheet properties, e.g., basis weight, caliper, strength, and stretch. Those of ordinary skill in the art will understand that a variety of engagements can be employed based on the above, as well as other factors. It is preferred that the engagement be chosen to substantially degrade the machine direction tensile strength of the web. It is further preferred that the engagement be at least 5 mils.

Where the element height, H, is about 42.5 mils and the elements have sidewall angles of from about 7° to 11°, the engagement range can be from about 16 to 32 mils. FIGS. 6A–6C depicts a 32 mil engagement, where the element heights are 42.5 mils and the sidewall angles are respectively 7°, 9°, and 11°. It is believed that lower sidewall angles make the process significantly easier to run with more controllability and decreased tendency to "picking".

Picking is the occurrence of fiber being left on the embossing roll or rolls as the web is embossed. Fiber on the roll can diminish the runability of the process for embossing the web, thereby interfering with embossing performance. When the performance of the embossing rolls is diminished to the point that the end product is not acceptable or the rolls are being damaged, it is necessary to stop the embossing process so that the embossing rolls can be cleaned. With any embossing process, there is normally a small amount of fiber left on the roll which does not interfere with the process if the roll is inspected periodically, e.g., weekly, and cleaned, if necessary. For purposes of the invention, we define picking as the deposition of fiber on the rolls at a rate that would require shut down for cleaning of the rolls more frequently than once a week.

The following examples exhibit the occurrence of picking observed in certain arrangements of cross-machine direction perforate embossed patterns. This data was generated during trials using steel embossing rolls engraved with the cross-machine direction beveled oval embossing pattern at three different sidewall angles. In particular, the embossing rolls were engraved with three separate regions on the rolls—a 7° embossing pattern, a 9° embossing pattern, and an 11° embossing pattern. Two trials were performed. In the first trial, the embossing rolls had an element height, H, of 45 mils. The basesheet, having a thickness of 6.4 mils, was embossed at engagements of 16, 24, and 32 mils. In the second trial, the steel rolls were modified by grinding 2.5 mils off the tops of the embossing elements, thereby reducing the element height to 42.5 mils and increasing the surface area of the element tops. The basesheet having a thickness of 6.2 mils was embossed at engagements of 16, 24, 28 and 32 mils. For each trial, embossing was performed in both half step and full step alignment.

Figure 9:
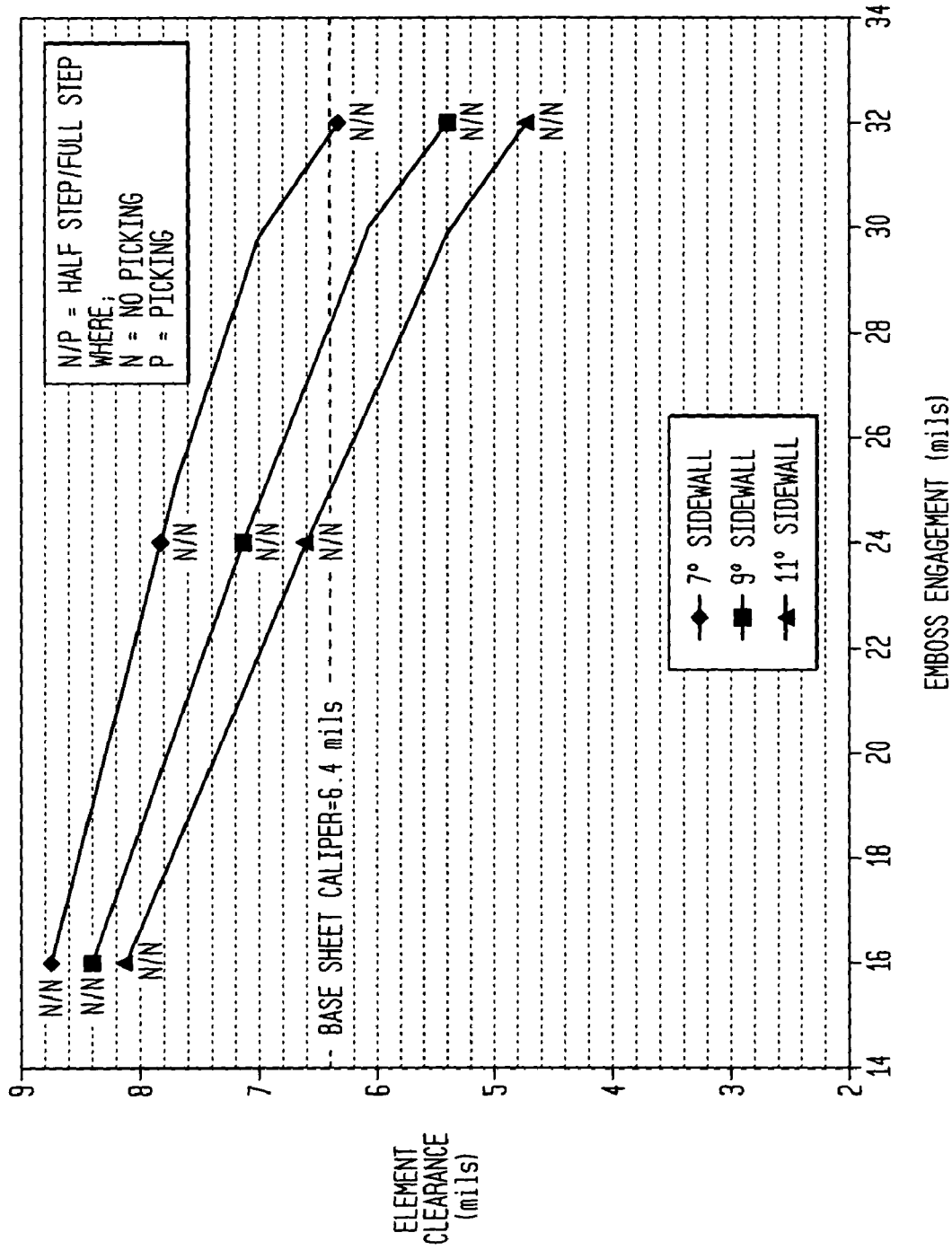
FIGS. 9 and 10 are plots of element clearance vs. emboss engagement illustrating picking tendencies and conditions.
Figure 10:
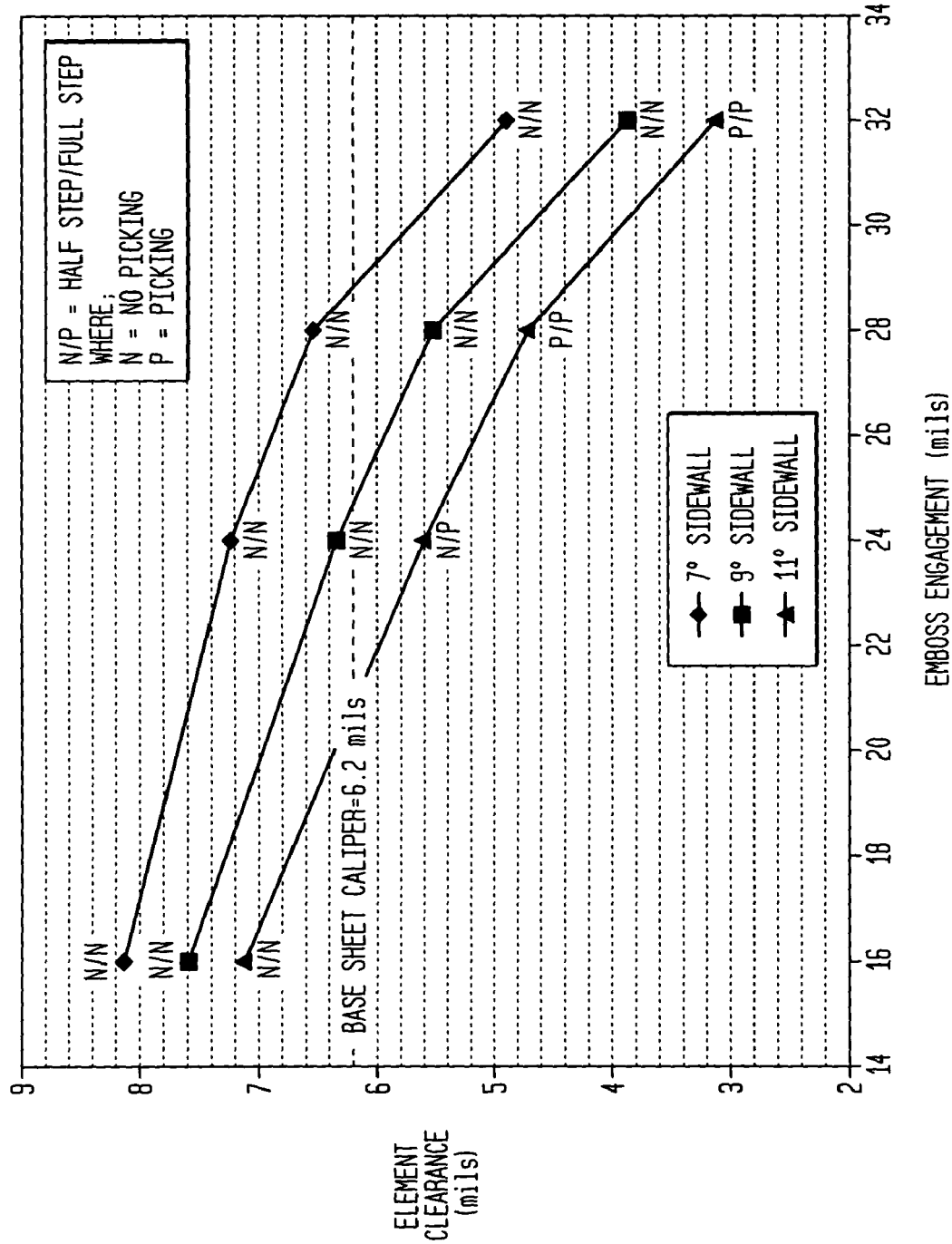

The element clearances for each of the sidewall angles of the first and second trials have been plotted against embossing engagement in FIGS. 9 and 10, respectively. The broken horizontal line on each plot indicates the caliper of a single ply of the basesheet that was embossed. The graphs have been annotated to show whether fiber picking was observed at each of the trial conditions (half step observation being to the left of the slash, full step observation to the right). The picking results are depicted in FIGS. 9 and 10, below.

FIG. 9 shows that for this particular trial using embossing rolls having a 45 mil element height, picking did not occur at any of the sidewall angles. However, as shown in FIG. 10, when the embossing rolls having a 42.5 mil element height were run, fiber picking was observed on the 11° sidewall angle elements at the higher embossing engagements, i.e., 24, 28, and 32 mils. No fiber picking was encountered with elements having sidewall angles of 7° or 9°.

Figure 7A:
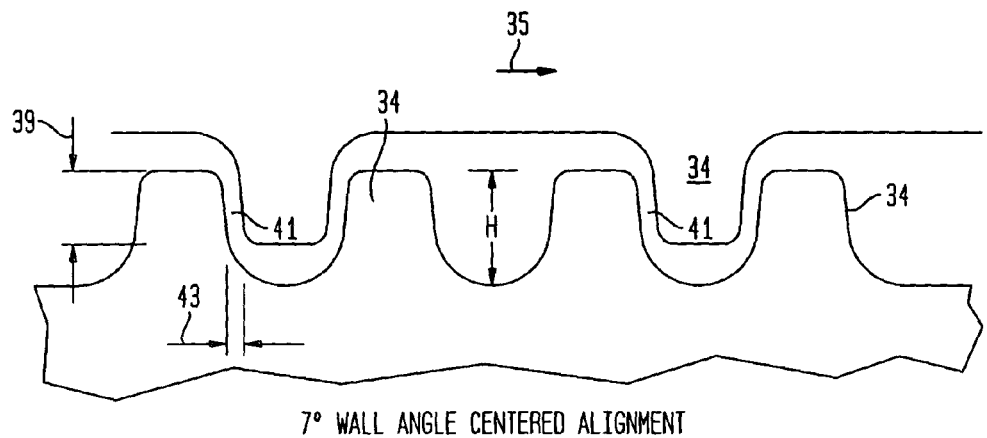
FIGS. 7A–7C are schematic side views of the cross-machine direction elements of embodiments of the present invention having differing wall angles and illustrating the effect of the differing wall angles.
Figure 7B:
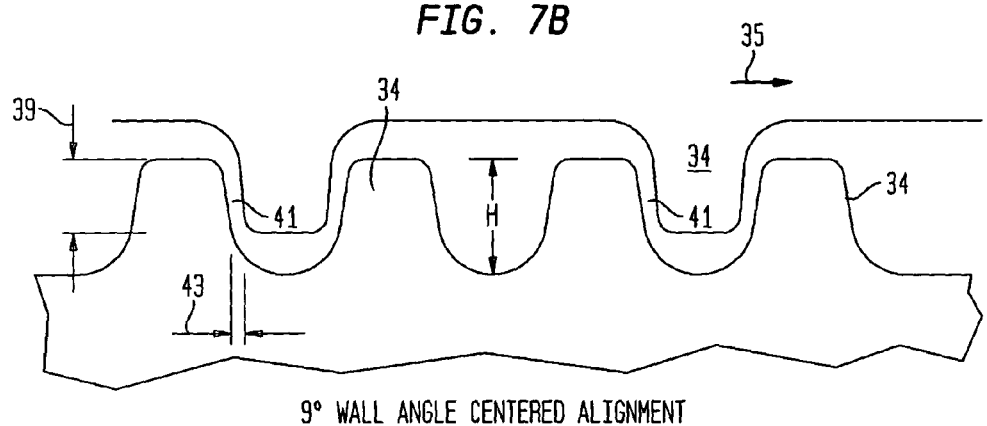
Figure 7C:
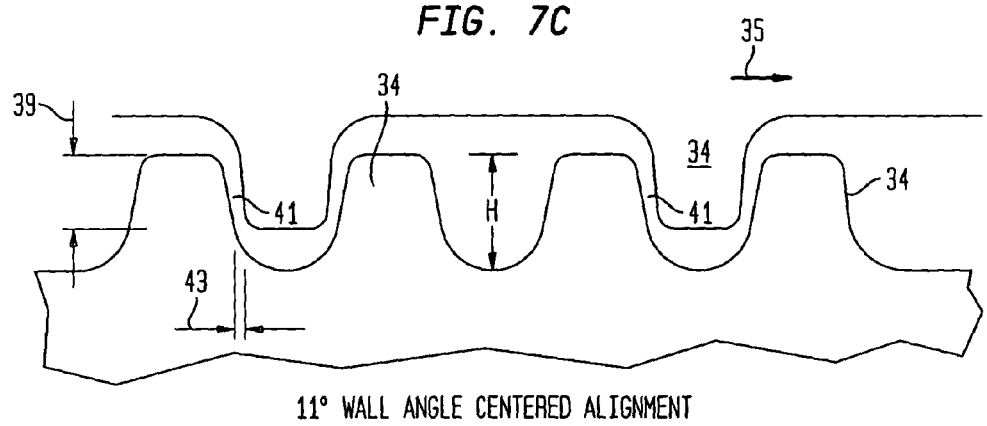
Figure 8A:
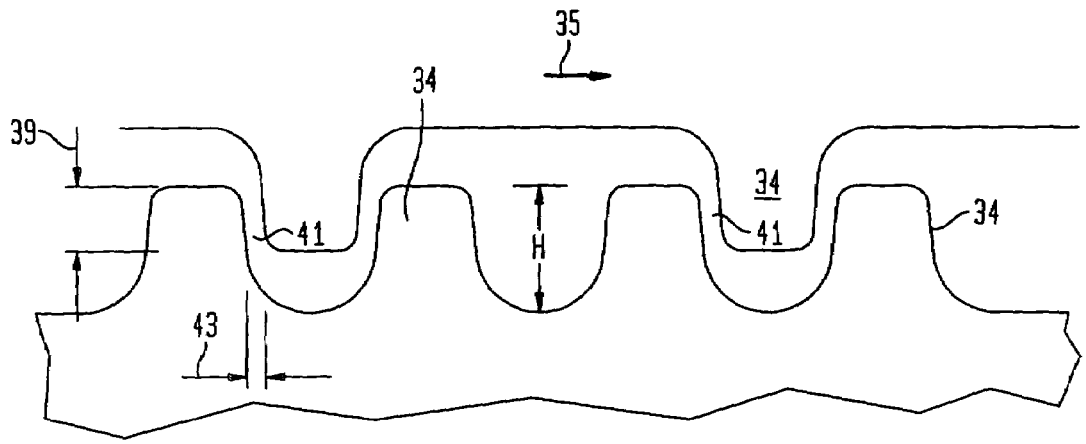
FIGS. 8A–8C are schematic side views of the cross-machine direction elements of yet another embodiment of the present invention having differing wall angles and illustrating the effect of the differing wall angles.
Figure 8B:
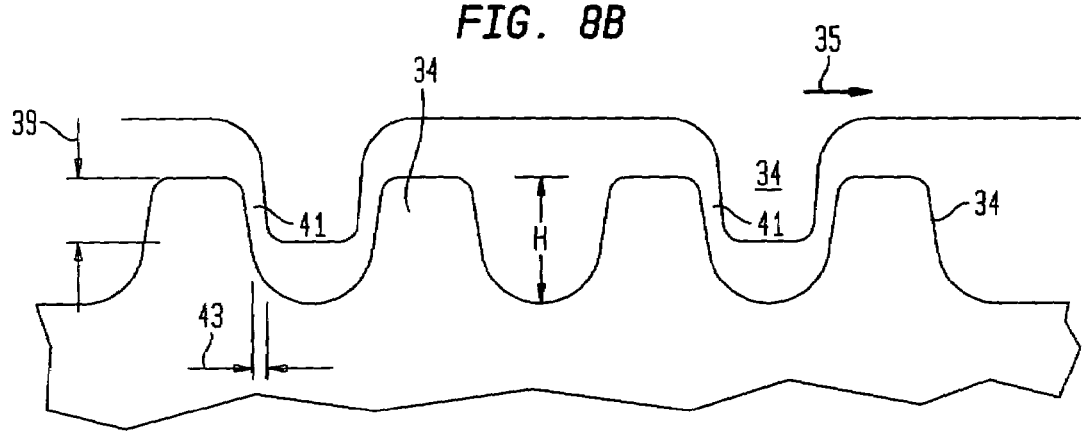
Figure 8C:
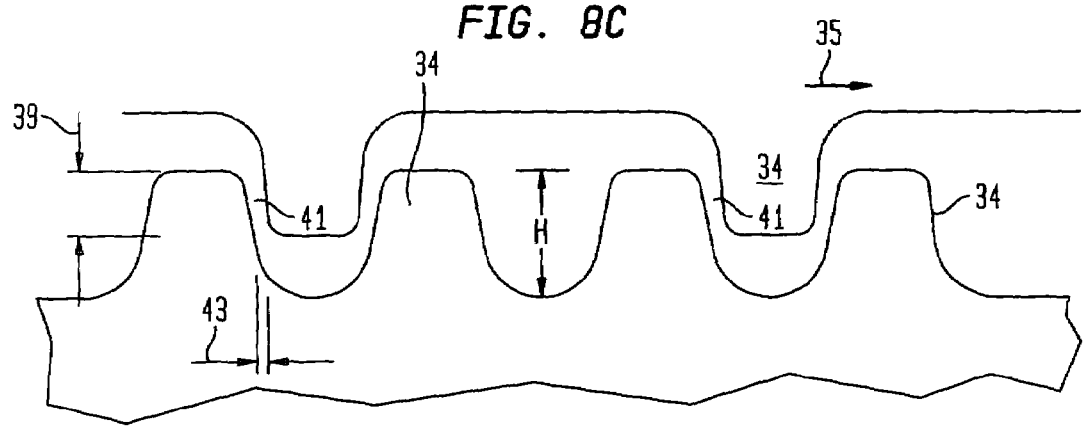

Based on the observed data, it appears that picking is a function of the element height, engagement, spacing, clearance, sidewall angle, alignment, and the particular physical properties of the basesheet, including basesheet caliper. An example of element clearance 43 can be seen in FIGS. 6A–6C, where the side profiles of the 42.5 mil elements (having 7°, 9°, and 11° sidewall angles) at 32 mil embossing engagement as shown. Clearance is the distance between adjacent engaging embossing elements. As noted above, the caliper of the embossed sheet for this trial was 6.2 mils. For the configuration shown in FIG. 6A, the calculated or theoretical clearance at 7° is 0.004906" (4.906 mils), the clearance at 9° is 0.003911" (3.911 mils), and the clearance at 11° is 0.00311" (3.11 mils) (FIG. 6B). Thus, for this trial at a 32 mil engagement, picking was observed only when the clearance was less than about ½ of the caliper of the sheet. Compare this to the clearance for the configuration shown in FIGS. 7A–7C. FIGS. 7A–7C depict the sidewall profiles of the 42.5 mil elements at 28 mil embossing engagement. In this arrangement, the calculated or theoretical clearance at 7° is 0.006535" (6.535 mils) (FIG. 7A), the clearance at 9° is 0.005540" (5.540 mils) (FIG. 7B), and the clearance at 11° is 0.004745" (4.745 mils) (FIG. 7C). In this trial, picking was observed when the clearance 43 was less than about ¾ of the caliper of the sheet. Note, however, that when embossing at 32 mils, as described above, picking did not occur at 9°, while the clearance was less than 4.745 mils. FIGS. 8A–8C depict the sidewall profiles of the 42.5 mil elements at 24 mil engagement. In this arrangement, the clearance at 11° is 00.005599" (5.599 mils) (FIG. 8C), slightly less than the caliper of the sheet. As shown in FIG. 10, picking did occur for these elements, but only when the elements were in full step alignment and not when in half step alignment. And, as shown in FIG. 10, picking did not occur at all, at any angle, engagement, or alignment, for the roll having elements 45 mils in height.

Thus, based on the collected data, picking can be controlled by varying element height, engagement, spacing, clearance, alignment, sidewall angle, roll condition, and the physical properties of the basesheet. Based upon the exemplified information, those of ordinary skill in the art will understand the effects of the various parameters and will be able to determine the various arrangements that will at least achieve a non-picking operation, i.e., the configuration required to avoid an unacceptable amount of picking based on the factors discussed above, and, hence, produce acceptable paper products with a process that does not require excessive downtime for roll cleaning.

Figure 11:
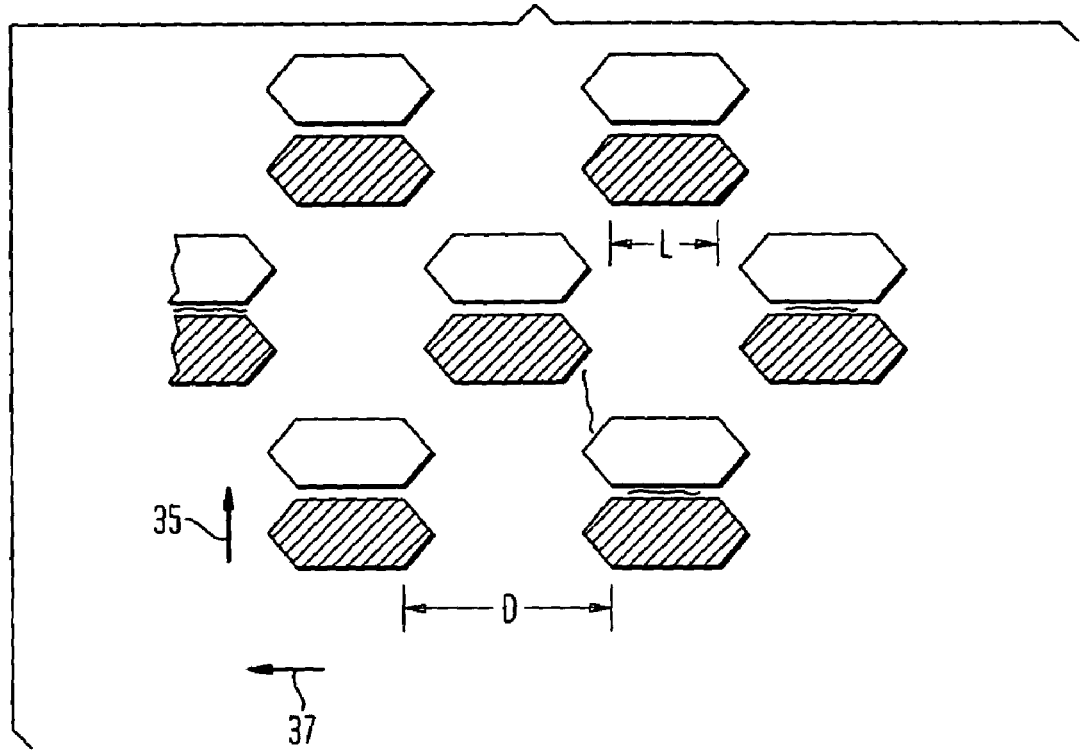
FIG. 11 illustrates the alignment of the cross-machine direction elements according to an embodiment of the present invention.
Figure 12:
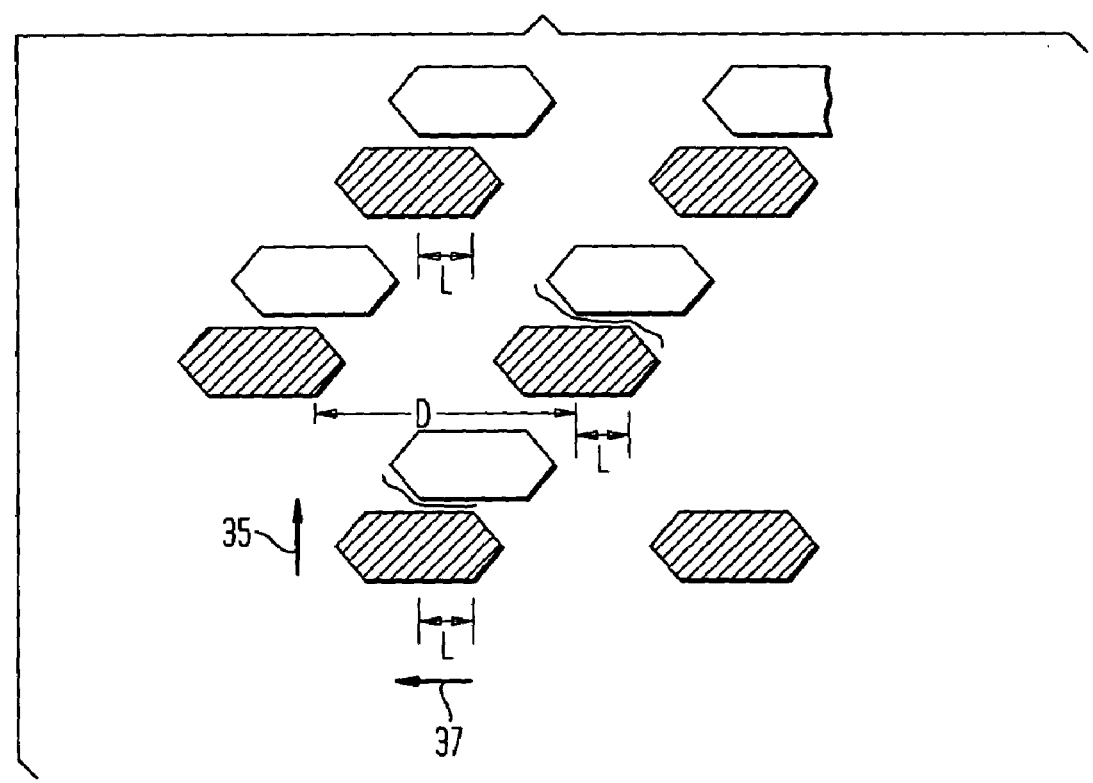
FIG. 12 illustrates the alignment of the cross-machine direction elements according to another embodiment of the present invention.
Figure 13:
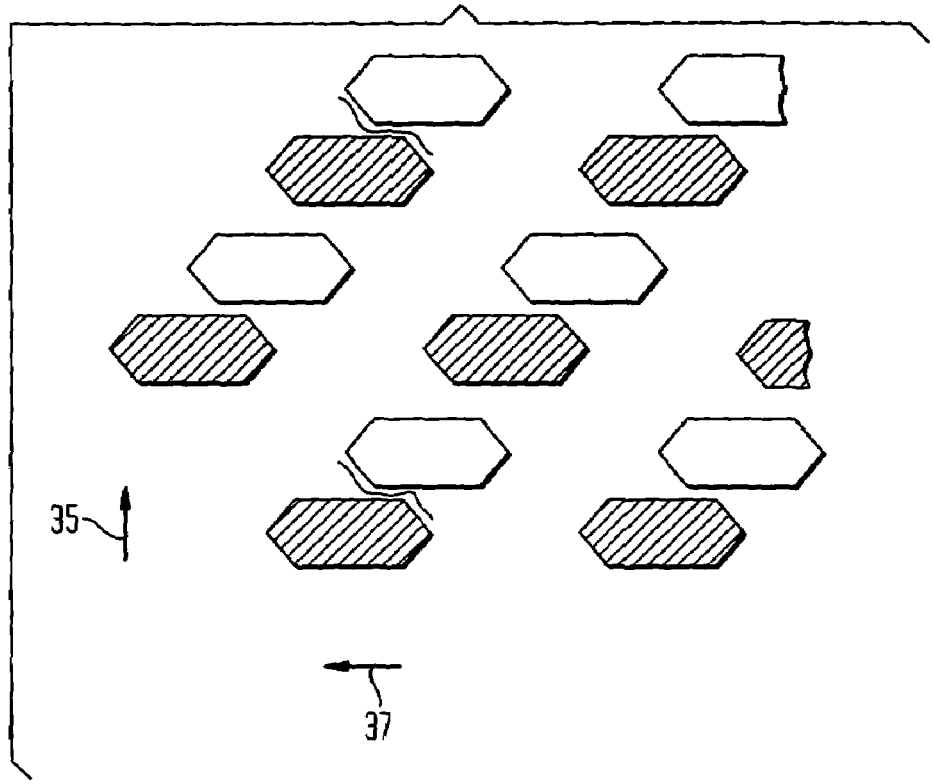
FIG. 13 illustrates the alignment of the cross-machine direction elements according to another embodiment of the present invention.
Figure 14:
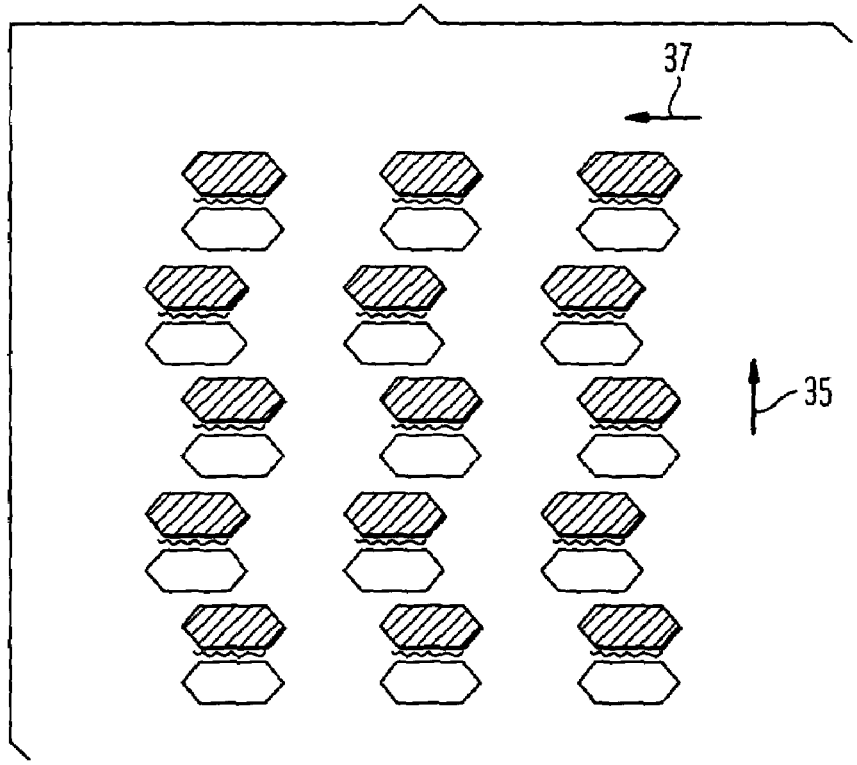
FIG. 14 illustrates the alignment of the cross-machine direction elements according to yet another embodiment of the present invention.

The element alignment affects the degradation of the web in the machine and cross-machine directions. Element alignment refers to the alignment in the cross-machine direction within the embossing element pairs when the embossing rolls are engaged. FIG. 11 depicts an embodiment including hexagonal embossing elements having a full step alignment, i.e., where the elements are completely overlapped in the cross-machine direction. FIG. 12 depicts an embodiment wherein hexagonal embossing elements are in half step alignment, i.e., where the elements of each element pair are staggered so that half of the engaged portion of their cross-machine direction dimensions overlap. FIG. 13 depicts an embodiment wherein hexagonal embossing elements are in quarter step alignment, i.e., where the elements of each element pair are staggered so that one quarter of the engaged portion of their cross-machine direction dimensions overlap. The embodiment depicted in FIG. 14 is a staggered array, wherein each element pair is in half step alignment with adjacent element pairs. Those of ordinary skill in the art will understand that a variety of element alignments are available for use with this invention, depending upon preferred embossing patterns, web strength requirements, and other factors.

It should further be appreciated from FIGS. 11 and 12 that the nip extends over a length, L, between embossing elements when they are engaged in the embossing position and the nips are then spaced apart a lateral or CD distance, D. Generally speaking, L is taken as the CD distance that the nip extends between two opposed embossing surfaces extending in the CD when the embossing elements are engaged, while D is the CD distance between adjacent nips along the CD (cross-machine direction). These parameters are best appreciated by reference to FIGS. 11 and 12; however, they may be estimated in many cases by reference to the corresponding dimensions of the embossing elements on the rolls; that is to say, L extends in the direction of distance 52 in FIG. 3 and D extends in the direction of distance 54 in FIG. 3 but will differ in actual dimensions when the elements are shaped as shown. When L and/or D vary over the height of the nip, L and D are determined as follows: L is the maximum length defined between two opposed CD embossing surfaces and D is the minimum CD distance between embossing nips. Thus, L and D are approximately equal to L' and D' in most cases as discussed in connection with FIG. 24 below. The inter-relationship between element geometry is readily appreciated by reference to FIGS. 3A through 3D. For opposed elements spaced a distance 54 of 0.015 inches or so, D may vary between about 0.096 and 0.056 inches or so depending upon engagement. Likewise, for opposed elements having an upper surface with a CD span of 0.047 inches and a base CD span 52 of 0.128 inches, L may vary between about 0.047 (0 engagement) and 0.09, which is where the nip is at a maximum at roughly the midpoint of the element heights when so engaged.

Figure 15A:
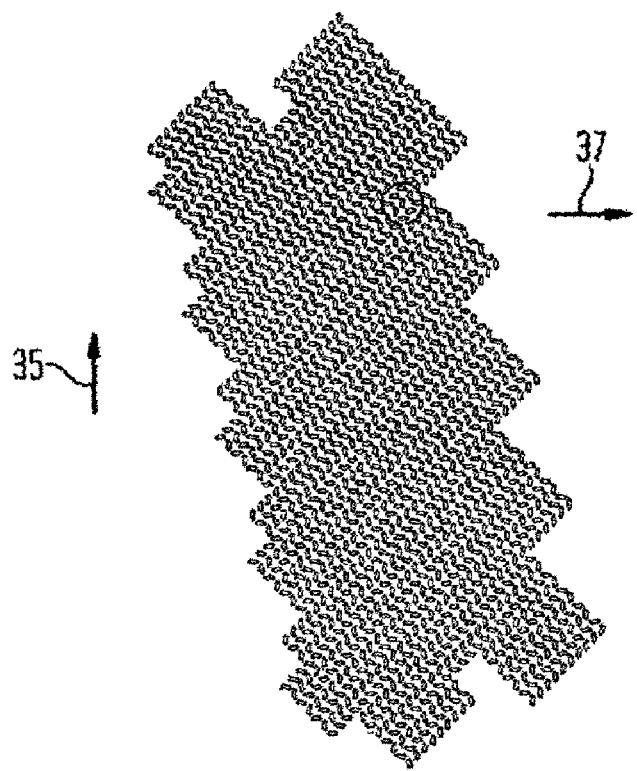
FIGS. 15A–15B illustrate embossing rolls having both cross-machine direction and machine direction elements according to an embodiment of the present invention.
Figure 15B:
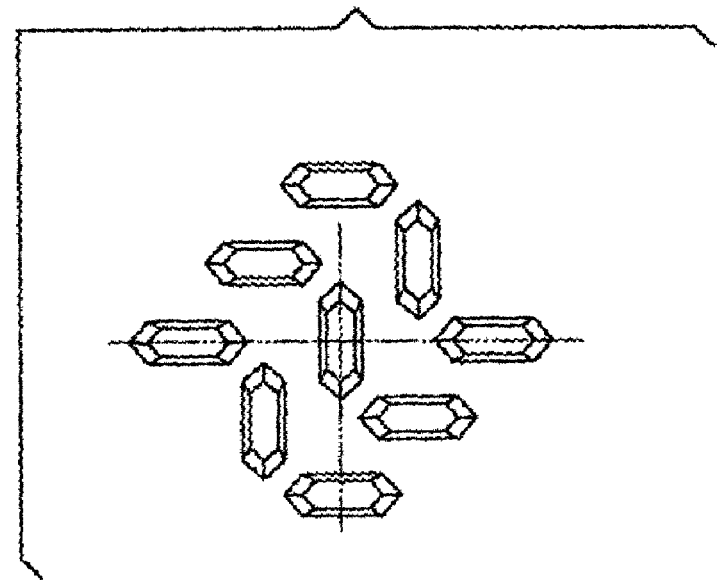

As noted above, the elements can be both in the machine direction and cross-machine direction. FIGS. 15A and 15B depict an emboss roll having cross-machine direction and machine direction hexagonal elements.

Figure 16:
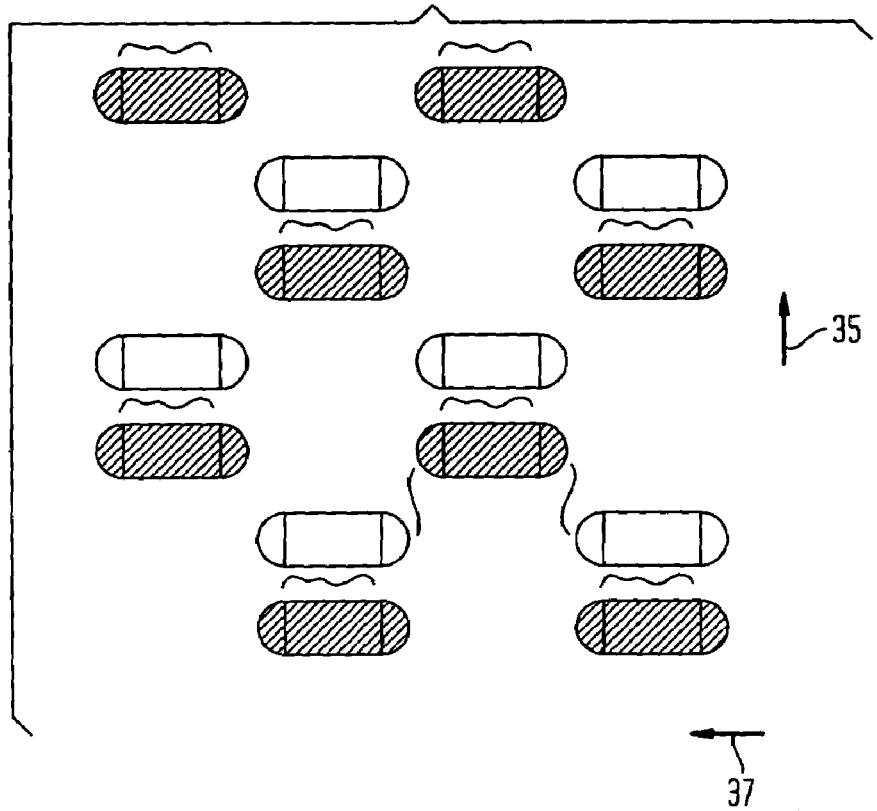
FIG. 16 illustrates the effect of cross-machine direction elements on a web according to yet another embodiment of the present invention.
Figure 17:
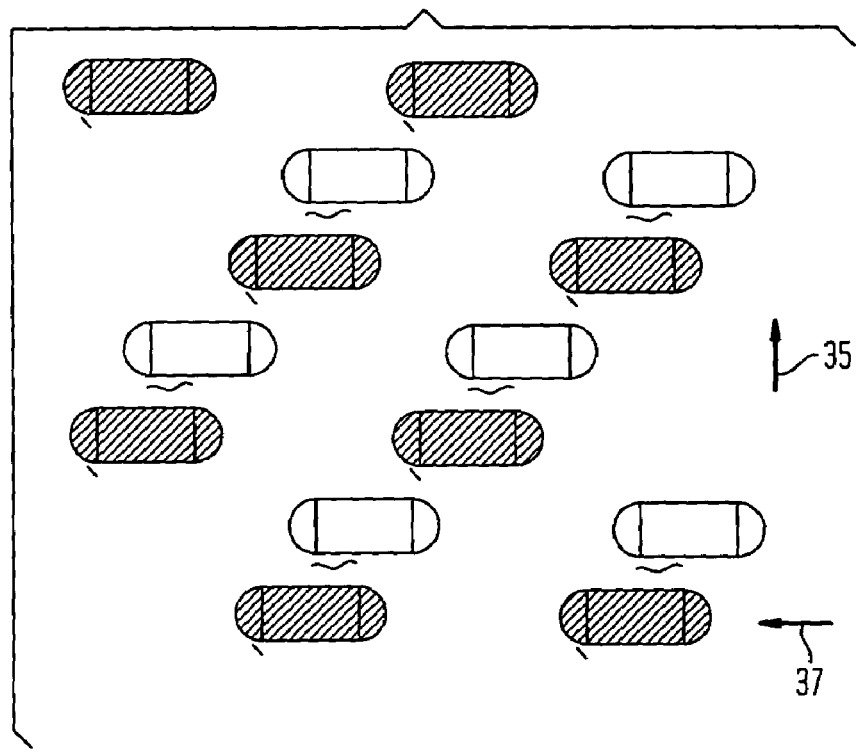
FIG. 17 illustrates the effect of cross-machine direction elements on a web according to yet another embodiment of the present invention.

In another embodiment, depicted in FIG. 16, beveled oval elements are in full step alignment. As with the full step hexagonal elements discussed above, in the area between the element pairs perforations exist primarily in the cross-machine direction. However, between the pairs of element pairs, perforations can be caused in the machine direction. The result is a degradation of strength in both the machine and cross-machine directions. In the embodiment depicted in FIG. 17, on the other hand, where the beveled oval elements in a half step alignment are employed, the machine direction perforations are substantially reduced. In particular, between the elements in half step alignment, the perforation lies primarily in the cross-machine direction. Between the element pairs, which are in zero step alignment, primarily pinpoint ruptures exist. These pinpoint ruptures have a minor effect on degradation of the directional properties of the web.

Those of ordinary skill in the art will understand that numerous different configurations of the above described element parameters, i.e., element shape, element orientation, sidewall angle, spacing, height, engagement, and alignment, can be employed in the present invention. The selection of each of these parameters may depend upon the basesheet used, the desired end product, or a variety of other factors.

To establish the effectiveness of the various element patterns in perforating the web in the cross-machine direction, and thereby degrading machine direction strength while maintaining cross-machine direction strength, a test was developed, the transluminance test, to quantify a characteristic of perforated embossed webs that is readily observed with the human eye. A perforated embossed web that is positioned over a light source will exhibit pinpoints of light in transmission when viewed at a low angle and from certain directions. The direction from which the sample must be viewed, e.g., machine direction or cross-machine direction, in order to see the light, is dependent upon the orientation of the embossing elements. Machine direction oriented embossing elements tend to generate machine direction ruptures in the web which can be primarily seen when viewing the web in the cross-machine direction. Cross-machine direction oriented embossing elements, on the other hand, tend to generate cross-machine direction ruptures in the web which can be seen primarily when viewing the web in the machine direction.

Figure 18:
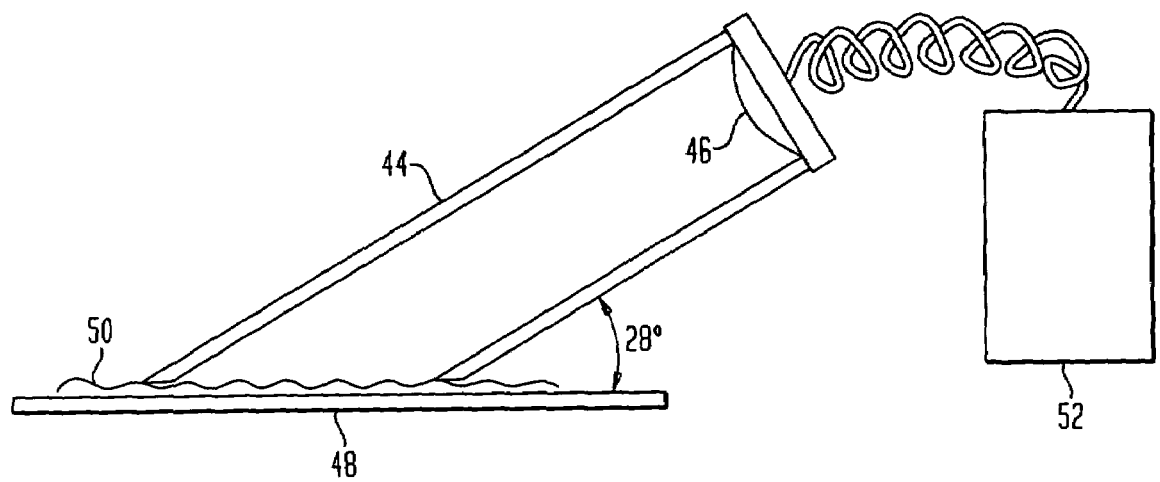
FIG. 18 depicts a transluminance test apparatus.

The transluminance test apparatus, as depicted in FIG. 18, consists of a piece of cylindrical tube 44 that is approximately 8.5" long and cut at a 28° angle. The inside surface of the tube is painted flat black to minimize the reflection noise in the readings. Light transmitted through the web itself, and not through a rupture, is an example of a non-target light source that could contribute to translucency noise which could lead other embossed webs to have transluminance ratios slightly exceeding 1.0, but typically by no more than about 0.05 points. A detector 46, attached to the non-angled end of the pipe, measures the transluminance of the sample. A light table 48, having a translucent glass surface, is the light source.

The test is performed by placing the sample 50 in the desired orientation on the light table 48. Detector 46 is placed on top of the sample 50 with the long axis of the tube 44 aligned with the axis of the sample 50, either the machine direction or cross-machine direction, that is being measured and the reading on a digital illuminometer 52 is recorded. The sample 50 is turned 90° and the procedure is repeated. This is done two more times until all four views, two in the machine direction and two in the cross-machine direction, are measured. In order to reduce variability, all four measurements are taken on the same area of the sample 50 and the sample 50 is always placed in the same location on the light table 48. To evaluate the transluminance ratio, the two machine direction readings are summed and divided by the sum of the two cross-machine direction readings.

To illustrate the results achieved when perforate embossing with cross-machine direction elements as compared to machine direction elements, a variety of webs were tested according to the above described transluminance test. The results of the test are shown in Table 1.

TABLE 1

Transluminance Ratios

| Basis Weight (lbs/ream) | Creping Method (Blade) | Emboss Alignment | Emboss Pattern | Transluminance Ratio |
|---|---|---|---|---|
| 30 | Undulatory | Full Step | CD Beveled Oval | 1.074 |
| 30 | Undulatory | Half Step | CD Beveled Oval | 1.056 |
| 32 | Undulatory | Half Step | CD Beveled Oval | 1.050 |
| 30 | Undulatory | Half Step | CD Oval | 1.047 |
| 31 | Undulatory | Half Step | CD Oval | 1.044 |
| 31 | Undulatory | Full Step | CD Oval | 1.043 |
| 30 | Undulatory | Full Step | CD Beveled Oval | 1.040 |
| 32 | Undulatory | Half Step | CD Beveled Oval | 1.033 |
| 30 | Undulatory | Half Step | CD Beveled Oval | 1.033 |
| 30 | Undulatory | Full Step | CD Oval | 1.027 |
| 32 | Undulatory | Half Step | CD Beveled Oval | 1.025 |
| 30 | Undulatory | Half Step | CD Oval | 1.022 |
| 31 | Undulatory | Full Step | CD Oval | 1.018 |
| 20 | Undulatory | Half Step | CD Beveled Oval | 1.015 |
| 30 | Undulatory | Half Step | CD Beveled Oval | 1.012 |
| 30 | Undulatory | Full Step | CD Beveled Oval | 1.006 |
| 28 | Standard | Unknown | MD Perforated | 1.000 |
| 24 | Undulatory | Half Step | MD Perforated | 0.988 |
| 22 | Standard | Unknown | MD Perforated | 0.980 |
| 29 | Undulatory | Half Step | MD Perforated | 0.966 |
| 29 | Undulatory | Half Step | MD Perforated | 0.951 |
| 31 | Undulatory | Half Step | MD Perforated | 0.942 |
| 29 | Undulatory | Half Step | MD Perforated | 0.925 |

A transluminance ratio of greater than 1.000 indicates that the majority of the perforations are in the cross-machine direction. For embossing rolls having cross-machine direction elements, the majority of the perforations are in the cross-machine direction. And, for the machine direction perforated webs, the majority of the perforations are in the machine direction. Thus, the transluminance ratio can provide a ready method of indicating the predominant orientation of the perforations in the web.

As noted above, perforated embossing in the cross-machine direction preserves cross-machine direction tensile strength. Thus, based on the desired end product, a web perforate embossed with a cross-machine direction pattern will exhibit one of the following when compared to the same basesheet embossed with a machine direction pattern: (a) a higher cross-machine direction tensile strength at equivalent finished product caliper, or (b) a higher caliper at equivalent finished product cross-machine direction tensile strength.

Furthermore, the tensile ratio (a comparison of the machine direction tensile strength to the cross-machine direction tensile strength—MD strength/CD strength) of the cross-machine perforate embossed web typically will be at or below the tensile ratio of the basesheet, while the tensile ratio of the sheet embossed using prior art machine direction perforate embossing typically will be higher than that of the basesheet. Dry tensile strengths (MD and CD) are measured with a standard Instron test device which may be configured in various ways, using for example, 3-inch wide strips of tissue or towel, conditioned at 50% relative humidity and 23° C. (73.4° F.), with the tensile test run at a crosshead speed of 2 in/min. Tensiles are sometimes reported in breaking length (BL, km). Wet tensile is measured by the Finch cup method or following generally the procedure for dry tensile, wet tensile is measured by first drying the specimens at 100° C. or so and then applying a 1½ inch band of water across the width of the sample with a Payne Sponge Device prior to tensile measurement. Wet/dry tensile ratios are simply ratios of the values determined by way of the foregoing methods.

Higher cross-machine direction strength at equivalent caliper is demonstrated in Table 2. This table compares two products perforate embossed from the same basesheet—a 29 pound per ream (lbs/R), undulatory blade-creped, conventional wet press (CWP) sheet.

TABLE 2

Increased CD Strength at Equivalent Caliper

| Emboss (perforate) | Basis Wt. (lbs/R) | Caliper (mils) | MD Dry Tensile (g/3") | CD Dry Tensile (g/3") | Dry Tensile Ratio (MD/CD) |
|---|---|---|---|---|---|
| CD Hexagonal | 29.1 | 144 | 3511 | 3039 | 1.16 |
| MD Hexagonal | 29.2 | 140 | 4362 | 1688 | 2.58 |

As shown in Table 2, the cross-machine direction perforate embossed web has approximately the same caliper as the machine direction perforate embossed web (144 vs. 140 mils, respectively), but its cross-machine direction dry tensile strength (3039 g/3") is considerably higher than that of the machine direction hexagonal-embossed web (1688 g/3"). In addition, compared to the tensile ratio of the basesheet (1.32, see Table 3, below), the cross-machine direction perforate embossed web has a lower ratio (1.16), while the machine direction perforate embossed web has a higher ratio (2.58). Thus the method of the present invention provides a convenient, low cost way of "squaring" the sheet—that is, bringing the tensile ratio closer to 1.0.

Higher caliper at equivalent finished product cross-machine direction tensile strength is illustrated by three examples presented in Table 3. For each example a common basesheet (identified above each data set) was perforate embossed with a cross-machine direction and a machine direction oriented pattern (Hollow Diamond is a machine direction oriented perforate emboss). Calipers reported herein are 8 sheet calipers unless otherwise indicated. The sheets are stacked and the caliper measurement taken about the central portion of the stack. Preferably, the test samples are conditioned in an atmosphere of 23°±1.0° C. (73.4°±1.8° F.) at 50% relative humidity for at least about 2 hours and then measured with a Thwing-Albert Model 89-II-JR or Progage Electronic Thickness Tester with 2-in (50.8-mm) diameter anvils, 539±10 grams dead weight load, and 0.231 in./sec descent rate.

TABLE 3

Increased Caliper at Equivalent CD Tensile Strength

| Emboss (perforate) | Basis Wt. (lbs/R) | Caliper (mils) | MD Dry Tensile (g/3") | CD Dry Tensile (g/3") | Dry Tensile Ratio (MD/CD) |
|---|---|---|---|---|---|
| Basesheet - undulatory blade-creped, CWP basesheet with tensile ratio = 1.32 | | | | | |
| CD Quilt | 28.8 | 108 | 4773 | 4068 | 1.17 |
| MD Quilt | 28.8 | 78 | 6448 | 3880 | 1.66 |
| Basesheet - undulatory blade-creped, CWP basesheet with tensile ratio = 1.32 | | | | | |
| CD Quilt | 29.5 | 154 | 2902 | 2363 | 1.23 |
| MD Quilt | 29.5 | 120 | 5361 | 2410 | 2.22 |
| Basesheet - undulatory blade-creped, CWP basesheet with tensile ratio = 1.94 | | | | | |
| CD Oval | 24.6 | 75 | 4805 | 2551 | 1.88 |
| Hollow Diamond | 24.1 | 56 | 5365 | 2364 | 2.27 |

In each case, the cross-machine direction perforate embossed product displays enhanced caliper at equivalent cross-machine direction dry tensile strength relative to its machine direction perforate embossed counterpart. Also, the cross-machine direction perforate embossed product has a lower tensile ratio, while the machine direction perforate embossed product has a higher tensile ratio, when compared to the corresponding basesheet.

The current invention further allows for a substantial reduction in base paper weight while maintaining the end product performance of a higher basis weight product. As shown in Table 4, wherein the web is formed of recycled fibers, the lower basis weight cross-machine direction perforate embossed towels achieved similar results to machine direction perforate embossed toweling made with higher basis weights.

TABLE 4

Performance Comparisons

| | PRODUCT ID | | | |
|---|---|---|---|---|
| | A | B | C | D |
| | EMBOSS | | | |
| | Hollow Diamond (MD Perforate) | CD Oval (CD Perforate) | Hollow Diamond (MD Perforate) | CD Oval (CD Perforate) |
| BASIS WT(LBS/REAM) | 24.1 | 22.2 | 31.3 | 28.9 |
| CALIPER | 56 | 62 | 76 | 81 |
| DRY MD TENSILE (g/3") | 5365 | 5057 | 5751 | 4144 |
| DRY CD TENSILE (g/3") | 2364 | 2391 | 3664 | 3254 |
| MD STRETCH (%) | 7.6 | 8.1 | 8.8 | 10.1 |
| CD STRETCH (%) | 6.3 | 6.1 | 5.5 | 5.3 |
| WET MD CURED TENSILE (g/3") | 1236 | 1418 | 1409 | 922 |
| WET CD CURED TENSILE (g/3") | 519 | 597 | 776 | 641 |
| MacBeth 3100 BRIGHTNESS (%) | 72.3 | 72.6 | 73.3 | 73.4 |
| SAT CAPACITY (g/m$^2$) | 98 | 102 | 104 | 119 |
| SINTECH MODULUS | 215 | 163 | 232 | 162 |
| BULK DENSITY | 367 | 405 | 340 | 385 |
| WET RESILIENCY (RATIO) | 0.735 | 0.725 | 0.714 | 0.674 |

In Table 4, two comparisons are shown. In the first comparison, a 24.1 lbs/ream machine direction perforated web is compared with a 22.2 lbs/ream cross-machine direction perforated web. Despite the basis weight difference of 1.9 lbs/ream, most of the web characteristics of the lower basis weight web are comparable to, if not better than, those of the higher basis weight web. For example, the caliper and the bulk density of the cross-machine direction perforated web are each about 10% higher than those of the machine direction perforated web. The wet and dry tensile strengths of the webs are comparable, while the Sintech modulus of the cross-machine direction perforated web (i.e., the tensile stiffness of the web, where a lower number is preferred) is considerably less than that of the machine direction perforated web. In the second comparison, similar results are achieved in the sense that comparable tensile ratios and physicals can be obtained with a lower basis weight web. Paradoxically, consumer data indicates that the D product was rated equivalent to the C product while the B product was at statistical parity with the A product, but was possibly slightly less preferred than the A product.

The invention is further appreciated by reference to Table 5 below which shows sheet properties, pre- and post-emboss. It is seen that Examples I through P embossed in accordance with the invention, exhibit much less CD tensile loss than other products where similar caliper gain is realized by embossing.

TABLE 5

Pre- and Post-Emboss Sheet Properties

| | Emboss | | | | | | | | |
|---|---|---|---|---|---|---|---|---|---|
| | Sheet E 10M | | | Sheet F Hollow Diamond | | | Sheet G Hollow Diamond | | |
| | BS* | FP** | % Change | BS* | FP** | % Change | BS* | FP** | % Change |
| Basis Weight (lbs/rm) | 26.1 | 26.1 | 0% | 26.2 | 26.1 | 0% | 25.7 | 26.2 | 2% |
| Caliper (mils/8 sheets) | 40.9 | 54.3 | 33% | 40.7 | 59.4 | 46% | 38.0 | 58.5 | 54% |
| Dry MD Tensile (g/3") | 6938 | 5658 | −18% | 6904 | 4432 | −36% | 7297 | 5365 | −26% |
| Dry CD Tensile (g/3") | 3516 | 2426 | −31% | 3560 | 2132 | −40% | 3457 | 2503 | −28% |
| MD Stretch (%) | 4.8 | 5.9 | 25% | 4.9 | 4.8 | −2% | 5.1 | 5.4 | 6% |
| CD Stretch (%) | 4.7 | 5.2 | 14% | 4.2 | 5.2 | 24% | 4.0 | 5.2 | 30% |
| MD TEA (mm-gmm^2) | 2.8 | 2.3 | −15% | 2.8 | 1.4 | −49% | 3.0 | 2.0 | −33% |
| CD TEA (mm-gm/mm^2) | 1.3 | 0.8 | −38% | 1.3 | 0.8 | −34% | 1.2 | 1.0 | −13% |
| Wet MD Cured Tensile (g/3") sponge | 1249 | 1110 | −11% | 1235 | 778 | −37% | 1530 | 1082 | −29% |
| Wet CD Cured Tensile (g/3") sponge | 614 | 445 | −27% | 573 | 377 | −34% | 647 | 493 | −24% |
| Wet MD Cured Tensile (g/3") Finch | 1270 | 932 | −25% | 1108 | 704 | −36% | 1306 | 904 | −31% |
| Wet CD Cured Tensile (g/3") Finch | 628 | 396 | −37% | 550 | 355 | −36% | 653 | 450 | −31% |
| WAR (seconds) (TAPPI) | 32 | 25 | −16% | 33 | 26 | −20% | 38 | 33 | −11% |
| MacBeth 3100 L* UV Excluded | 91.2 | 91.3 | 0% | 91.1 | 91.3 | 0% | | 91.4 | |
| MacBeth 3100 A* UV Excluded | −1.3 | −1.3 | −6% | −1.3 | −1.2 | −8% | | −1.5 | |
| MacBeth 3100 B* UV Excluded | 6.2 | 5.8 | −6% | 6.6 | 6.2 | −6% | | 6.0 | |
| MacBeth 3100 Brightness (%) UV Excluded | 71.7 | 72.4 | 1% | 71.0 | 72.0 | 1% | | 72.3 | |
| MacBeth 3100 - Opacity (%) | 76.6 | 76.9 | 0% | 76.3 | 76.4 | 0% | | 76.8 | |
| SAT Capacity (g/m^2) | 113 | 122 | 7% | 117 | 135 | 15% | 107 | 128 | 20% |
| SAT Time (seconds) | 624 | 369 | −41% | 610 | 414 | −32% | 645 | 619 | −4% |
| SAT Rate (g/sec^0.5) | 0.0113 | 0.0116 | 2% | 0.0122 | 0.0111 | −9% | 0.0105 | 0.0080 | −24% |
| Sintech Modulus | 263 | 181 | −30% | 273 | 164 | −40% | 246 | 150 | −39% |
| Void Volume Wt Inc (%) | 366 | 366 | 0% | 344 | 387 | 13% | 324 | 401 | 24% |
| Wet Resiliency Energy Ratio (Ratio) | 0.847 | 0.728 | −14% | 0.831 | 0.707 | −15% | 0.793 | 0.700 | −12% |

TABLE 5-continued

Pre- and Post-Emboss Sheet Properties

| | | | | | | | | | |
|---|---|---|---|---|---|---|---|---|---|
| Wet Resiliency Springback (Ratio) | 0.853 | 0.784 | −8% | 0.853 | 0.703 | −18% | 0.852 | 0.734 | −14% |
| Wet Resiliency Wet Comp Bulk (cm^3/g) | 3.20 | 3.19 | 0% | 3.21 | 3.23 | 1% | 3.19 | 3.21 | 1% |
| Stack Height (inches) | | | | | | | | 5.29 | |
| Free-Standing Stack Height (inches) | | | | | | | | 5.41 | |
| Compressed Stack Height (inches) | | | | | | | | 5.13 | |
| Stack Compression (%) | | | | | | | | 5.20 | |
| Sheet Length (inches) | | | | | | | | 9.57 | |
| Sheet Width (inches) | | | | | | | | 9.35 | |
| Folded Sheet Width (inches) | | | | | | | | 3.21 | |
| Folded Sheet Length (inches) | | | | | | | | 9.35 | |

| | Emboss | | | | | | | | |
|---|---|---|---|---|---|---|---|---|---|
| | Sheet H Hollow Diamond | | | Sheet I (full step) CD Oval | | | Sheet J (full step) CD Oval | | |
| | BS* | FP** | % Change | BS* | FP*** | % Change | BS* | FP** | % Change |
| Basis Weight (lbs/rm) | 23.9 | 24.1 | 1% | 21.7 | 21.5 | −1% | 22.6 | 22.9 | 1% |
| Caliper (mils/8 sheets) | 34.6 | 65.2 | 89% | 34.9 | 59.9 | 72% | 48.0 | 61.0 | 27% |
| Dry MD Tensile (g/3") | 6003 | 4896 | −19% | 6062 | 4578 | −24% | 7022 | 5639 | −20% |
| Dry CD Tensile (g/3") | 3215 | 1934 | −40% | 2847 | 2366 | −17% | 3604 | 3041 | −16% |
| MD Stretch (%) | 8.0 | 7.6 | −4% | 10.5 | 10.0 | −5% | 5.6 | 6.1 | 8% |
| CD Stretch (%) | 4.2 | 5.6 | 33% | 4.4 | 4.6 | 5% | 5.8 | 6.8 | 18% |
| MD TEA (mm-gmm^2) | 4.3 | 2.5 | −42% | 5.2 | 3.1 | −40% | 3.6 | 2.5 | −30% |
| CD TEA (mm-gm/mm^2) | 1.2 | 0.9 | −26% | 1.0 | 0.8 | −18% | 1.6 | 1.6 | −8% |
| Wet MD Cured Tensile (g/3") sponge | 1113 | 810 | −26% | 936 | 704 | −25% | 1579 | 1294 | −18% |
| Wet CD Cured Tensile (g/3") sponge | 500 | 324 | −35% | 389 | 315 | −19% | 818 | 699 | −15% |
| Wet MD Cured Tensile (g/3") Finch | 825 | 702 | −6% | 885 | 612 | −31% | 1798 | 1165 | −35% |
| Wet CD Cured Tensile (g/3") Finch | 425 | 306 | −28% | 405 | 282 | −30% | 955 | 662 | −31% |
| WAR (seconds) (TAPPI) | 79 | 55 | −30% | 114 | 113 | −1% | 61 | 59 | −3% |
| MacBeth 3100 L* UV Excluded | 88.2 | 88.7 | 1% | 87.8 | 88.0 | 0% | 89.6 | 90.0 | 0% |
| MacBeth 3100 A* UV Excluded | −1.0 | −0.2 | −85% | −1.3 | −0.6 | −55% | −1.3 | −1.2 | −5% |
| MacBeth 3100 B* UV Excluded | 5.1 | 2.7 | −47% | 4.9 | 2.9 | −40% | 6.9 | 6.1 | −11% |
| MacBeth 3100 Brightness (%) UV Excluded | 66.9 | 70.4 | 5% | 66.3 | 68.7 | 4% | 67.6 | 69.3 | 3% |
| MacBeth 3100 - Opacity (%) | 71.8 | 71.8 | 0% | 74.3 | 83/0 | 0% | 73.0 | 74.6 | 2% |

TABLE 5-continued

Pre- and Post-Emboss Sheet Properties

| | | | | | | | | | |
|---|---|---|---|---|---|---|---|---|---|
| SAT Capacity (g/m$^2$) | 95.8 | 141.4 | 47% | 77.5 | 113.9 | 47% | 110.4 | 100.0 | −9% |
| SAT Time (seconds) | 868 | 579 | −31% | 838 | 574 | −32% | 924 | 229 | −75% |
| SAT Rate (g/sec$^{0.5}$) | 0.0081 | 0.0053 | −37% | 0.060 | 0.0067 | 11% | 0.087 | 0.0060 | −31% |
| Sintech Modulus | 204 | 127 | −37% | 230 | 155 | −33% | 202 | 173 | −14% |
| Void Volume Wt Inc (%) | 376 | 415 | 14% | 341 | 373 | 9% | 387 | 375 | −3% |
| Wet Resiliency Energy Ratio (Ratio) | | | | | | | | | |
| Wet Resiliency Springback (Ratio) | | | | | | | | | |
| Wet Resiliency Wet Comp Bulk (cm$^3$/g) | | | | | | | | | |
| Stack Height (inches) | | 5.30 | | | 5.00 | | | 5.36 | |
| Free-Standing Stack Height (inches) | | 5.47 | | | 5.25 | | | 5.56 | |
| Compressed Stack Height (inches) | | 5.12 | | | 4.85 | | | 5.13 | |
| Stack Compression (%) | | 6.39 | | | 7.62 | | | 7.81 | |
| Sheet Length (inches) | | 9.45 | | | 9.55 | | | 9.57 | |
| Sheet Width (inches) | | 6.22 | | | 9.31 | | | 9.26 | |
| Folded Sheet Width (inches) | | 3.18 | | | 3.18 | | | 3.27 | |
| Folded Sheet Length (inches) | | 9.28 | | | 9.34 | | | 9.26 | |

| | Emboss | | | | | | | | |
|---|---|---|---|---|---|---|---|---|---|
| | Sheet K (half step) CD Oval | | | Sheet L (full step) CD Oval | | | Sheet M (full step) CD Oval | | |
| | BS* | FP** | % Change | BS* | FP** | % Change | BS* | FP** | % Change |
| Basis Weight (lbs/rm) | 25.9 | 25.9 | 0% | 25.9 | 26.2 | 1% | 26.3 | 26.2 | 0% |
| Caliper (mils/8 sheets) | 41.9 | 56.2 | 34% | 41.9 | 56.5 | 35% | 39.1 | 59.8 | 54% |
| Dry MD Tensile (g/3") | 6323 | 5519 | −13% | 6323 | 5469 | −14% | 7274 | 5623 | −23% |
| Dry CD Tensile (g/3") | 3172 | 2668 | −16% | 3172 | 2747 | −13% | 3703 | 3005 | −19% |
| MD Stretch (%) | 5.1 | 5.6 | 9% | 5.1 | 5.7 | 10% | 5.0 | 5.7 | 13% |
| CD Stretch (%) | 4.3 | 4.9 | 14% | 4.3 | 4.7 | 10% | 4.5 | 4.7 | 8% |
| MD TEA (mm-gmm$^2$) | 2.6 | 2.2 | −18% | 2.6 | 2.2 | −17% | 3.0 | 2.1 | −31% |
| CD TEA (mm-gm/mm$^2$) | 1.1 | 1.0 | −7% | 1.1 | 1.0 | −7% | 1.3 | 1.1 | −17% |
| Wet MD Cured Tensile (g/3") sponge | 1080 | 930 | −14% | 1080 | 917 | −15% | 1239 | 975 | −21% |
| Wet CD Cured Tensile (g/3") sponge | 549 | 446 | −19% | 549 | 440 | −20% | 598 | 492 | −18% |
| Wet MD Cured Tensile (g/3") Finch | 892 | 855 | −4% | 892 | 809 | −9% | 1060 | 836 | −21% |
| Wet CD Cured Tensile (g/3") Finch | 516 | 432 | −16% | 516 | 451 | −13% | 574 | 451 | −21% |
| WAR (seconds) (TAPPI) | 22 | 25 | 12% | 22 | 23 | 5% | 46 | 38 | −15% |

TABLE 5-continued

Pre- and Post-Emboss Sheet Properties

| | | | | | | | | | |
|---|---|---|---|---|---|---|---|---|---|
| MacBeth 3100 L* UV Excluded | 90.9 | 91.2 | 0% | 90.9 | 91.1 | 0% | | 91.1 | |
| MacBeth 3100 A* UV Excluded | −1.3 | −1.3 | −2% | −1.3 | −1.3 | −2% | | −1.2 | |
| MacBeth 3100 B* UV Excluded | 6.3 | 6.2 | −2% | 6.3 | 6.2 | −2% | | 5.4 | |
| MacBeth 3100 Brightness (%) UV Excluded | 71.0 | 71.7 | 1% | 71.0 | 71.6 | 1% | | 72.4 | |
| MacBeth 3100 - Opacity (%) | 75.9 | 76.5 | 1% | 75.9 | 76.5 | 1% | | 76.5 | |
| SAT Capacity (g/m^2) | 121 | 133 | 9% | 121 | 131 | 8% | 115 | 138 | 21% |
| SAT Time (seconds) | 759 | 796 | 5% | 759 | 818 | 8% | 798 | 853 | 14% |
| SAT Rate (g/sec^0.5) | 0.014 | 0.015 | 10% | 0.014 | 0.014 | 4% | 0.0111 | 0.0092 | −22% |
| Sintech Modulus | 275 | 222 | −19% | 275 | 228 | −17% | 333 | 203 | −38% |
| Void Volume Wt Inc (%) | 357 | 379 | 6% | 357 | 365 | 2% | 331 | 361 | 9% |
| Wet Resiliency Energy Ratio (Ratio) | 0.737 | 0.676 | −8% | 0.737 | 0.671 | −9% | 0.743 | 0.698 | −6% |
| Wet Resiliency Springback (Ratio) | 0.842 | 0.764 | −9% | 0.842 | 0.772 | −8% | 0.848 | 0.761 | −10% |
| Wet Resiliency Wet Comp Bulk (cm^3/g) | 3.25 | 5.42 | 67% | 3.25 | 3.23 | −1% | 3.11 | 3.13 | 0% |
| Stack Height (inches) | | 5.19 | | | 5.20 | | | 5.25 | |
| Free-Standing Stack Height (inches) | | 5.23 | | | 5.23 | | | 5.40 | |
| Compressed Stack Height (inches) | | 5.06 | | | 5.05 | | | 5.08 | |
| Stack Compression (%) | | 3.16 | | | 3.43 | | | 5.96 | |
| Sheet Length (inches) | | 9.58 | | | 9.53 | | | 9.47 | |
| Sheet Width (inches) | | 9.42 | | | 9.38 | | | 9.44 | |
| Folded Sheet Width (inches) | | 3.29 | | | 3.28 | | | 3.23 | |
| Folded Sheet Length (inches) | | 9.38 | | | 9.37 | | | 9.35 | |

| | Emboss | | | | | | | | |
|---|---|---|---|---|---|---|---|---|---|
| | Sheet N (full step) CD Oval | | | Sheet O (full step) CD Oval | | | Sheet P (full step) CD Oval | | |
| | BS* | FP** | % Change | BS* | FP** | % Change | BS* | FP** | % Change |
| Basis Weight (lbs/rm) | 26.2 | 25.7 | −2% | 22.5 | 22.5 | 0% | 24.3 | 24.1 | −0.8% |
| Caliper (mils/8 sheets) | 39.5 | 53.8 | 36% | 41.0 | 58.3 | 42% | 37.7 | 57.4 | 52.3% |
| Dry MD Tensile (g/3") | 7778 | 5712 | −27% | 6374 | 4322 | −32% | 5616 | 4831 | −13.6% |
| Dry CD Tensile (g/3") | 4096 | 3196 | −22% | 3006 | 2234 | −26% | 3004 | 2452 | −18.3% |
| MD Stretch (%) | 5.3 | 6.0 | 13% | 3.6 | 3.9 | 8% | 7.8 | 8.1 | 4.0% |
| CD Stretch (%) | 4.3 | 4.5 | 7% | 4.7 | 4.9 | 4% | 4.1 | 4.2 | 3.7% |
| MD TEA (mm-gmm^2) | 3.4 | 2.2 | −36% | 2.0 | 1.2 | −40% | 3.5 | 2.7 | −18.9% |

TABLE 5-continued

Pre- and Post-Emboss Sheet Properties

| | | | | | | | | | |
|---|---|---|---|---|---|---|---|---|---|
| CD TEA (mm-gm/mm^2) | 1.5 | 1.2 | −24% | 1.1 | 0.8 | −26% | 0.9 | 0.7 | −20.3% |
| Wet MD Cured Tensile (g/3") sponge | 1248 | 992 | −21% | 953 | 615 | −35% | 986 | 751 | −23.3% |
| Wet CD Cured Tensile (g/3") sponge | 658 | 543 | −17% | 422 | 291 | −31% | 432 | 363 | −15.4% |
| Wet MD Cured Tensile (g/3") Finch | 1180 | 908 | −23% | 708 | 608 | −14% | 792 | 660 | −14.4% |
| Wet CD Cured Tensile (g/3") Finch | 602 | 508 | −13% | 380 | 288 | −24% | 373 | 300 | −19.1% |
| WAR (seconds) (TAPPI) | 49 | 52 | 7% | 67 | 46 | −32% | 75 | 68 | −5.8% |
| MacBeth 3100 L* UV Excluded | | 90.9 | | | 76.0 | | | 75.2 | 75.3 | 0.2% |
| MacBeth 3100 A* UV Excluded | | −1.4 | | | 0.5 | | | 0.9 | 0.9 | |
| MacBeth 3100 B* UV Excluded | | 5.5 | | | 9.8 | | | 10.6 | 10.7 | 1.2% |
| MacBeth 3100 Brightness (%) UV Excluded | | 72.0 | | | 41.5 | | | 39.9 | 40.0 | 0.3% |
| MacBeth 3100 - Opacity (%) | | 76.0 | | | 88.1 | | | 86.4 | 87.0 | 0.7% |
| SAT Capacity (g/m^2) | 108 | 123 | 13% | 105 | 122 | 16% | 102.5 | 114.3 | 12.2% |
| SAT Time (seconds) | 669 | 639 | −4% | 637 | 521 | −18% | 501 | 344 | −30.2% |
| SAT Rate (g/sec^0.5) | 0.010 | 0.0085 | −15% | 0.0107 | 0.011 | 3% | 0 | 0 | −32.7% |
| Sintech Modulus | 298 | 157 | −47% | 232 | 200 | −14% | 244.53 | 145.64 | −39.1% |
| Void Volume Wt Inc (%) | 312 | 369 | 18% | 399 | 423 | 6% | 350 | 387 | 10.7% |
| Wet Resiliency Energy Ratio (Ratio) | | | | 0.824 | 0.763 | −7% | 1 | | |
| Wet Resiliency Springback (Ratio) | | | | 0.862 | 0.771 | −11% | 0.806 | | |
| Wet Resiliency Wet Comp Bulk (cm^3/g) | | | | 3.53 | 3.55 | 1% | 2.867 | | |
| Stack Height (inches) | | 5.17 | | | 5.26 | | | | | |
| Free-Standing Stack Height (inches) | | 5.30 | | | 5.44 | | | | | |
| Compressed Stack Height (inches) | | 4.96 | | | 5.03 | | | | | |
| Stack Compression (%) | | 6.51 | | | 7.43 | | | | | |
| Sheet Length (inches) | | 9.58 | | | 9.57 | | | | | |
| Sheet Width (inches) | | 9.32 | | | 9.31 | | | | | |
| Folded Sheet Width (inches) | | 9.31 | | | 3.25 | | | | | |
| Folded Sheet Length (inches) | | 3.23 | | | 9.31 | | | | | |

*BS = Unembossed Basesheet
**FP = Finished Product

As will be appreciated from the foregoing, the CD embossing technique of the present invention is especially advantageous for use on biaxially undulatory basesheet as described in U.S. Pat. No. 5,690,788, the disclosure of which is incorporated herein by reference and described briefly below in connection with FIGS. 19 through 23.

Figure 19:
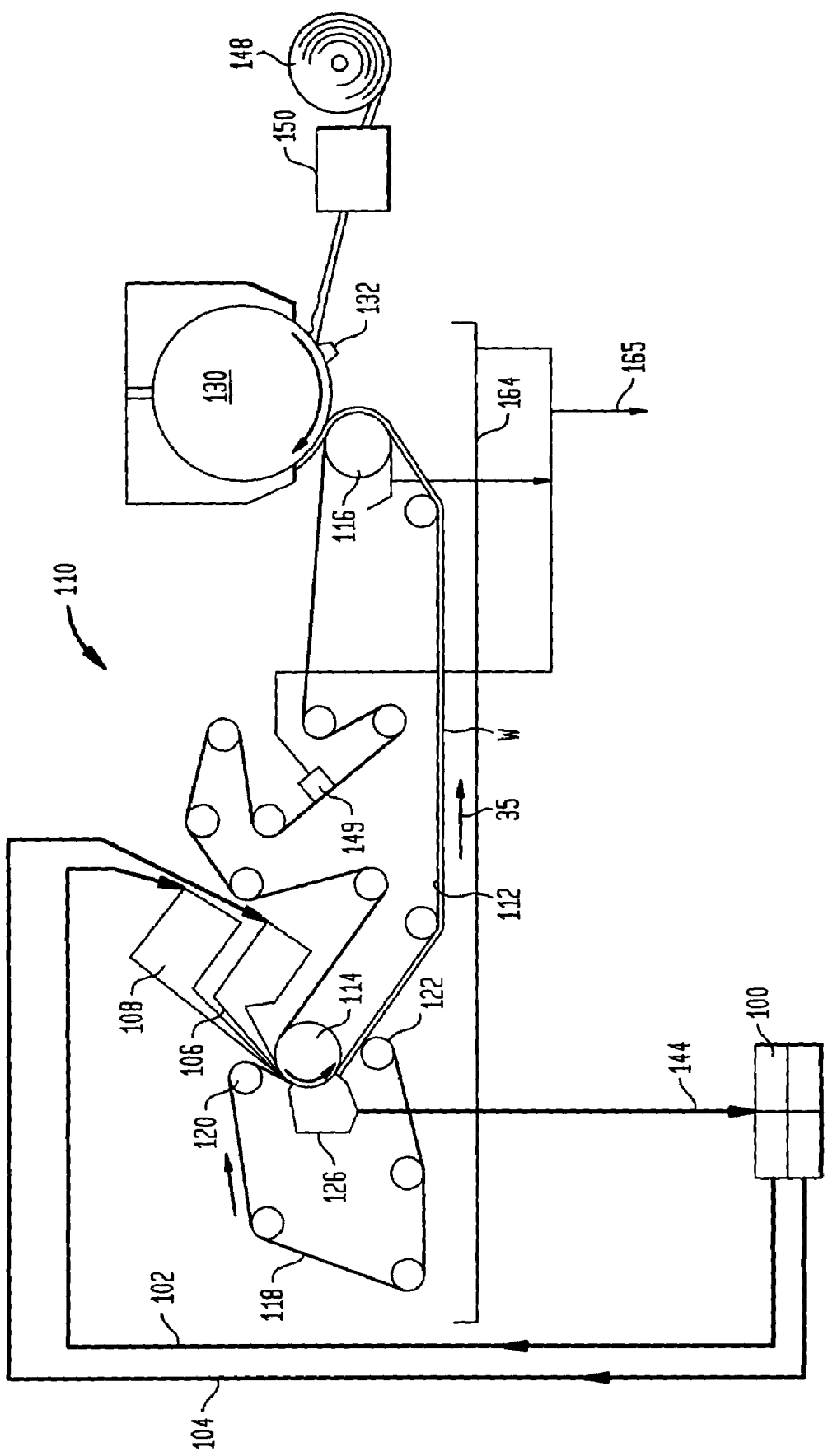
FIG. 19 is a schematic diagram of a papermachine useful for making a web with MD ridges.

FIG. 19 illustrates a papermachine wherein a machine chest 100, which may be compartmentalized, is used for preparing furnishes that are treated with chemicals having different functionality depending on the character of the various fibers used. This embodiment shows two head boxes thereby making it possible to produce a stratified product. The product according to the present invention can be made with single or multiple head boxes and regardless of the number of head boxes may be stratified or unstratified. The treated furnish is transported through different conduits 102 and 104, where they are delivered to the head box 106, 108 (indicating an optionally compartmented headbox) of a crescent forming machine 110.

FIG. 19 shows a web-forming end or wet end with a liquid permeable foraminous support member 112 which may be of any conventional configuration. Foraminous support member 112 may be constructed of any of several known materials including photopolymer fabric, felt, fabric, or a synthetic filament woven mesh base with a very fine synthetic fiber batt attached to the mesh base. The foraminous support member 112 is supported in a conventional manner on rolls, including breast roll 114 and couch or pressing roll, 116.

Forming wire 118 is supported on rolls 120 and 122 which are positioned relative to the breast roll 114 for pressing the wire 118 to converage on the foraminous support member 112. The foraminous support member 112 and the wire 118 move in the same direction and at the same speed which is in the direction of rotation of the breast roll 114. The pressing wire 114 and the foraminous support member 112 converge at an upper surface of the forming roll 114 to form a wedge-shaped space or nip into which one or more jets of water or foamed liquid fiber dispersion (furnish) provided by single or multiple headboxes 106, 108 is pressed between the pressing wire 118 and the foraminous support member 112 to force fluid through the wire 118 into a saveall 126 where it is collected to reuse in the process.

The nascent web, W, formed in the process is carried by the foraminous support member 112 to the pressing roll 116 where the nascent web, W, is transferred to the drum 130 of a Yankee dryer. Fluid is pressed from the web, W, by pressing roll 116 as the web is transferred to the drum 130 of a dryer where it is partially dried and preferably wet-creped by means of an undulatory creping blade 132. The wet-creped web is then transferred to an after-drying section 150 prior to being collected on a take-up roll 148. The drying section 150 may include through-air dryers, impingement dryers, can dryers, another Yankee dryer and the like as is well known in the art and discussed further below.

A pit 164 is provided for collecting water squeezed from the furnish by the press roll 116. The water collected in pit 164 may be collected into a flow line 165 for separate processing to remove surfactant and fibers from the water and to permit recycling of the water back to the papermaking machine 110.

An absorbent paper web can be made by dispersing fibers into aqueous slurry and depositing the aqueous slurry onto the forming wire of a papermaking machine. Any suitable forming scheme might be used. For example, an extensive but non-exhaustive list includes a crescent former, a C-wrap twin wire former, an S-wrap twin wire former, a suction breast roll former, a Fourdrinier former, or any art-recognized forming configuration. The forming fabric can be any suitable foraminous member including single layer fabrics, double layer fabrics, triple layer fabrics, photopolymer fabrics, and the like. Non-exhaustive background art in the forming fabric area includes U.S. Pat. Nos. 4,157,276; 4,605,585; 4,161,195; 3,545,705; 3,549,742; 3,858,623; 4,041,989; 4,071,050; 4,112,982; 4,149,571; 4,182,381; 4,184,519; 4,314,589; 4,359,069; 4,376,455; 4,379,735; 4,453,573; 4,564,052; 4,592,395; 4,611,639; 4,640,741; 4,709,732; 4,759,391; 4,759,976; 4,942,077; 4,967,085; 4,998,568; 5,016,678; 5,054,525; 5,066,532; 5,098,519; 5,103,874; 5,114,777; 5,167,261; 5,199,261; 5,199,467; 5,211,815; 5,219,004; 5,245,025; 5,277,761; 5,328,565; and 5,379,808 all of which are incorporated herein by reference in their entirety. One forming fabric particularly useful is Voith Fabrics Forming Fabric 2164 made by Voith Fabrics Corporation, Shreveport, La.

Foam-forming of the aqueous furnish on a forming wire or fabric may be employed as a means for controlling the permeability or void volume of the sheet upon wet-creping. Suitable foam-forming techniques are disclosed in U.S. Pat. No. 4,543,156 and Canadian Patent No. 2,053,505, the disclosures of which are incorporated herein by reference.

Figure 20:
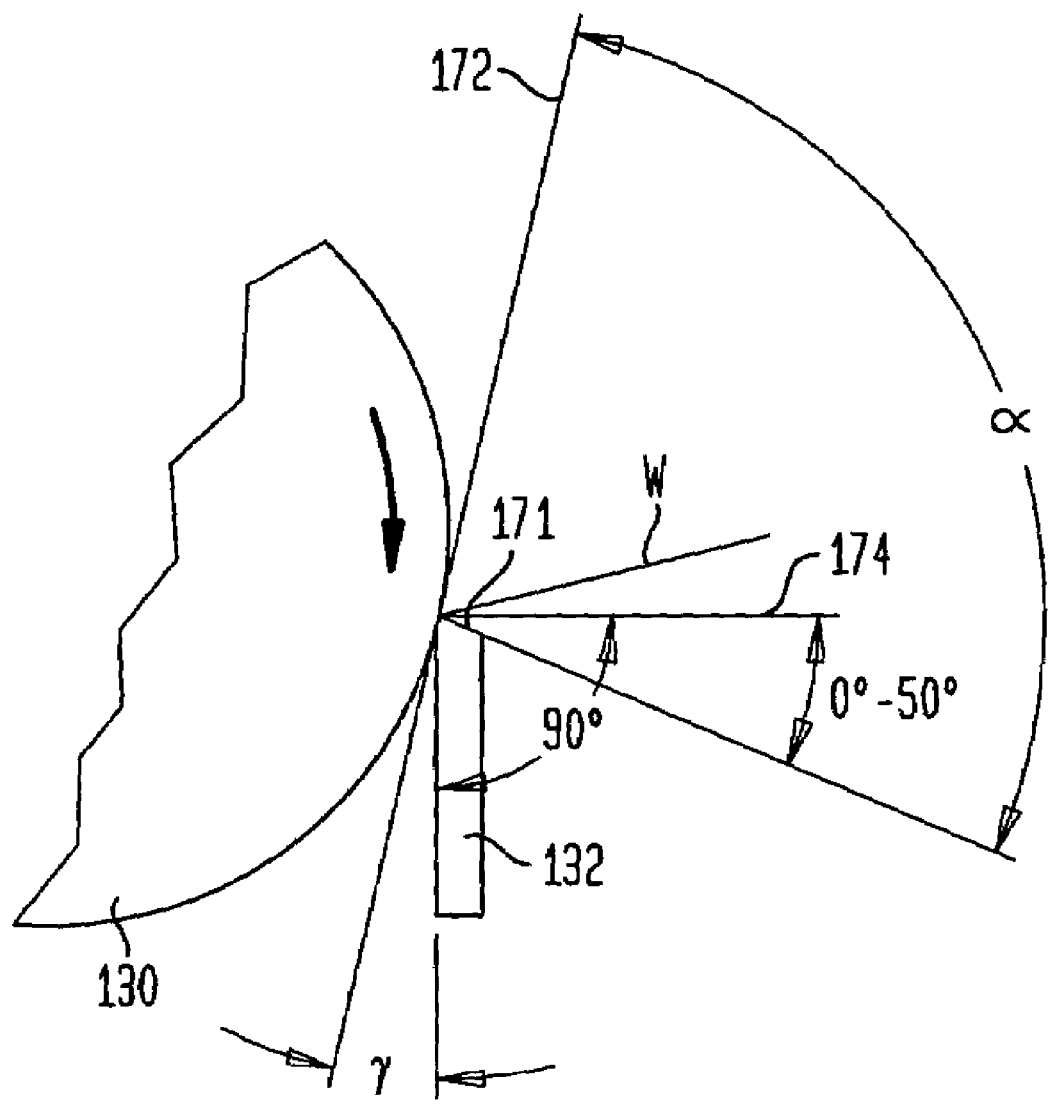
FIG. 20 is a schematic diagram illustrating creping angles for producing a creped web which may be embossed in accordance with the invention.

The creping angle and blade geometry may be employed as means to influence the sheet properties. Referring to FIG. 20, the creping angle or pocket angle, $\alpha$, is the angle that the creping rake surface 171 makes with a tangent 172 to a Yankee dryer at the line of contact of the creping blade 132 with the rotating cylinder 130 as in FIG. 19. So also, an angle $\gamma$ is defined as the angle the blade body makes with tangent 172, whereas the bevel angle of creping blade 132 is the angle surface 171 defines with a perpendicular 174 to the blade body as shown in the diagram. Referring to FIG. 20, the creping angle is readily calculated from the formula:

$$\alpha = 90 + \text{blade bevel angle} - \gamma$$

for a conventional blade. These parameters vary over the creping surface of an undulatory blade as discussed herein.

In accordance with the present invention, creping of the paper from a Yankee dryer is carried out using an undulatory creping blade, such as that disclosed in U.S. Pat. No. 5,690,788, the disclosure of which is incorporated by reference. Use of the undulatory crepe blade has been shown to impart several advantages when used in production of tissue products. In general, tissue products creped using an undulatory blade have higher caliper (thickness), increased CD stretch, and a higher void volume than do comparable tissue products produced using conventional crepe blades. All of these changes effected by use of the undulatory blade tend to correlate with improved softness perception of the tissue products. These blades, together with high-lignin pulps, cooperate to provide unexpected and, indeed, dramatic synergistic effect as discussed in connection with the examples below.

FIGS. 21A through 21D illustrate a portion of a preferred undulatory creping blade 190 useable in the practice of the present invention in which a relief surface extends indefinitely in length, typically exceeding 100 inches in length and often reaching over 26 feet in length to correspond to the width of the Yankee dryer on the larger modern papermachines. Flexible blades of the patented undulatory blade having indefinite length can suitably be placed on a spool and used on machines employing a continuous creping system. In such cases the blade length would be several times the width of the Yankee dryer. In contrast, the height of the blade 190 is usually on the order of several inches while the thickness of the body is usually on the order of fractions of an inch.

As illustrated in FIGS. 21A through 21D, an undulatory cutting edge 193 of the patented undulatory blade is defined by serrations 196 disposed along, and formed in, one edge of a surface 192 so as to define an undulatory engagement surface. Cutting edge 193 is preferably configured and dimensioned so as to be in continuous undulatory engagement with Yankee 130 when positioned as shown in FIG. 20, that is, the blade continuously contacts the Yankee cylinder in a sinuous line generally parallel to the axis of the Yankee cylinder. In particularly preferred embodiments, there is a continuous undulatory engagement surface 200 having a plurality of substantially colinear rectilinear elongate regions 202 adjacent a plurality of crescent shaped regions 204 about a foot 206 located at the upper portion of the side 208 of the blade which is disposed adjacent the Yankee. Undulatory surface 200 is thus configured to be in continuous surface-to-surface contact over the width of a Yankee cylinder when in use as shown in FIGS. 19 and 20 in an undulatory or sinuous wave-like pattern.

The number of teeth per inch may be taken as the number of elongate regions 202 per inch and the tooth depth is taken as the height, H, of the groove indicated at 201 adjacent surface 208.

Several angles are used in order to describe the geometry of the cutting edge of the undulatory blade. To that end, the following terms are used:

Creping angle "$\alpha$"—the angle between a rake surface 198 of the blade 190 and the plane tangent to the Yankee at the point of intersection between the undulatory cutting edge 193 and the Yankee;

Axial rake angle "$\beta$"—the angle between the axis of the Yankee and the undulatory cutting edge 193 which is the curve defined by the intersection of the surface of the Yankee with indented rake surface of the blade 190;

Relief angle "$\gamma$"—the angle between the relief surface 192 of the blade 190 and the plane tangent to the Yankee at the intersection between the Yankee and the undulatory cutting edge 193, the relief angle measured along the flat portions of the present blade is equal to what is commonly called "blade angle" or holder angle", that is "$\gamma$" in FIG. 20.

Quite obviously, the value of each of these angles will vary depending upon the precise location along the cutting edge at which it is to be determined. The remarkable results achieved with the undulatory blades of the patented undulatory blade in the manufacture of the absorbent paper products are due to those variations in these angles along the cutting edge. Accordingly, in many cases it will be convenient to denote the location at which each of these angles is determined by a subscript attached to the basic symbol for that angle. As noted in the '788 patent, the subscripts "f", "c" and "m" refer to angles measured at the rectilinear elongate regions, at the crescent shaped regions, and the minima of the cutting edge, respectively. Accordingly, "$\gamma_f$", the relief angle measured along the flat portions of the present blade, is equal to what is commonly called "blade angle" or "holder angle". In general, it will be appreciated that the pocket angle $\alpha_f$ at the rectilinear elongate regions is typically higher than the pocket angle $\alpha_c$ at the crescent shaped regions.

Figure 21E:
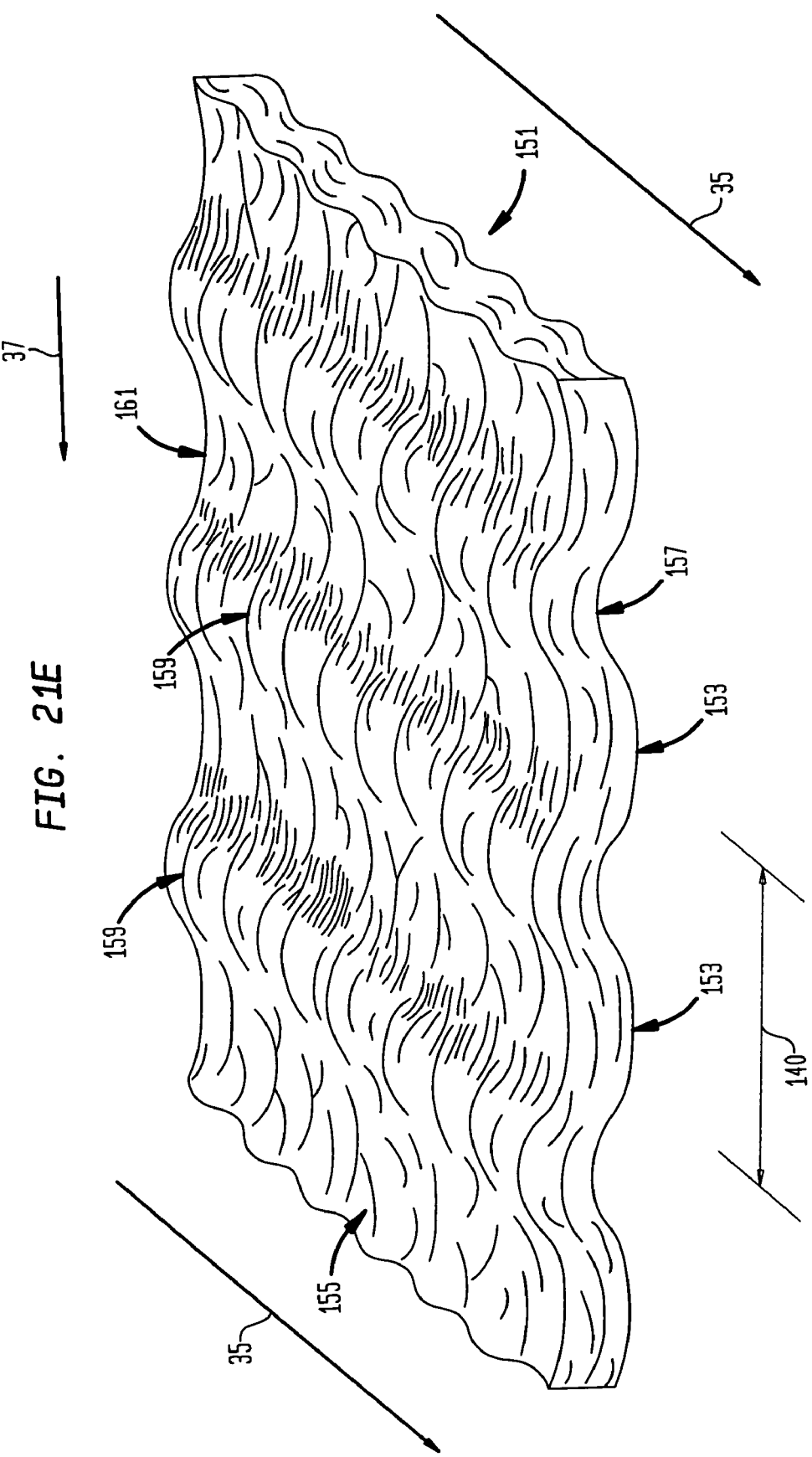
FIGS. 21A–21D illustrate an undulatory creping blade which may be used to produce a creped biaxially undulatory web shown in FIG. 21E which may be embossed in accordance with the invention.

An undulatory creping blade may be used to produce a creped or recreped web as shown in FIG. 21E comprising a biaxially undulatory cellulosic fibrous web 151 creped from a Yankee dryer 130 shown in FIGS. 19 and 20, characterized by a reticulum of intersecting crepe bars 155, and undulations defining ridges 153 extending in the machine direction 35 on the air side thereof, said crepe bars 155 extending transversely in the cross-machine direction, the web 151 having furrows 157 between ridges 153 on the air side as well as crests 159 disposed on the Yankee side of the web opposite furrows 157 and sulcations 161 interspersed between crests 159 and opposite to ridges 153, wherein the spatial frequency of said transversely extending crepe bars 155 is from about 10 to about 150 crepe bars per inch, and the spatial frequency of said longitudinally extending ridges 153 is from about 4 to about 50 ridges per inch. The distance between ridges 140 is taken as the center-to-center distance between adjacent ridges. This distance is the inverse of the frequency, F, of the machine direction ridges in the cross direction 37. For a product made with a creping blade with 12 teeth per inch, the frequency, F, is 12 ridges/inch and the distance 140 is $\frac{1}{12}$". It should be understood that strong calendering of the sheet can significantly reduce the height of ridges 153, making them difficult to perceive by the eye, without loss of the beneficial effects.

The crepe frequency count for a creped basesheet or product may be measured with the aid of a microscope. The Leica Stereozoom.RTM. 4 microscope has been found to be particularly suitable for this procedure. The sheet sample is placed on the microscope stage with its Yankee side up and the cross direction of the sheet vertical in the field of view. Placing the sample over a black background improves the crepe definition. During the procurement and mounting of the sample, care should be taken that the sample is not stretched. Using a total magnification of 18–20, the microscope is then focused on the sheet. An illumination source is placed on either the right or left side of the microscope stage, with the position of the source being adjusted so that the light from it strikes the sample at an angle of approximately 45 degrees. It has been found that Leica or Nicholas Illuminators are suitable light sources. After the sample has been mounted and illuminated, the crepe bars are counted by placing a scale horizontally in the field of view and counting the crepe bars that touch the scale over a one-half centimeter distance. This procedure is repeated at least two times using different areas of the sample. The values obtained in the counts are then averaged and multiplied by the appropriate conversion factor to obtain the crepe frequency in the desired unit length.

It should be noted that the thickness of the portion of web 151 between longitudinally extending crests 159 and furrows 157 will on the average typically be bout 5% greater than the thickness of portions of web 151 between ridges 153 and sulcations 161. Suitably, the portions of web 151 adjacent longitudinally extending ridges 153 (on the air side) are about from about 1% to about 7% thinner than the thickness of the portion of web 151 adjacent to furrows 157 as defined on the air side of web 151.

The height of ridges 153 correlates with the tooth depth, H, formed in undulatory creping blade 190. At a tooth depth of about 0.010 inches, the ridge height is usually from about 0.0007 to about 0.003 inches for sheets having a basis weight of 14–19 pounds per ream. At double the depth, the ridge height increases to 0.005 to 0.008 inches. At tooth depths of about 0.030 inches, the ridge height is about 0.010 to 0.013 inches. At higher undulatory depth, the height of ridges 153 may not increase and could in fact decrease. The height of ridges 153 also depends on the basis weight of the sheet and strength of the sheet.

Advantageously, the average thickness of the portion of web 151 adjoining crests 159 is significantly greater than the thickness of the portions of web 151 adjoining sulcations 161; thus, the density of the portion of web 151 adjacent crests 159 can be less than the density of the portion of web 151 adjacent sulcations 161. The process of the present invention produces a web having a specific caliper of from about 2 to about 8 mils per 8 sheets per pound of basis weight. The usual basis weight of web 151 is from about 7 to about 35 lbs/3000 sq. ft. ream.

Suitably, when web 151 is calendered, the specific caliper of web 151 is from about 2.0 to about 6.0 mils per 8 sheets per pound of basis weight and the basis weight of said web is from about 7 to about 35 lbs/3000 sq. ft. ream.

While the products of the invention may be made by way of a dry-crepe process, a wet crepe process is preferred in some embodiments, particularly with respect to single-ply towel in some cases. When a wet-crepe process is employed, after-drying section 150 may include an impingement air dryer, a through-air dryer, a Yankee dryer or a plurality of can dryers. Impingement-air dryers are disclosed in the following patents and applications, the disclosure of which is incorporated herein by reference:

U.S. Pat. No. 5,865,955 of Ilvespaaet et al.
U.S. Pat. No. 5,968,590 of Ahonen et al.
U.S. Pat. No. 6,001,421 of Ahonen et al.
U.S. Pat. No. 6,119,362 of Sundqvist et al.
U.S. patent application Ser. No. 09/733,172, entitled "Wet Crepe, Impingement-Air Dry Process for Making Absorbent Sheet", now U.S. Pat. No. 6,432,267

When an impingement-air after dryer is used, after drying section 150 of FIG. 19 may have the configuration shown in FIG. 22.

There is shown in FIG. 22 an impingement air dry apparatus 150 useful in connection with the present invention. The web is creped off of a Yankee dryer, such as Yankee dryer 130 of FIG. 19 utilizing a creping blade 132. The web, W, is aerodynamically stabilized over an open draw utilizing an air foil 220 as generally described in U.S. Pat. No. 5,891,309 to Page et al., the disclosure of which is incorporated herein by reference. Following a transfer roll 222, web, W, is disposed on a transfer fabric 224 and subjected to wet shaping by way of an optional blow box 226 and vacuum shoe 228. The particular conditions and impression fabric selected depend on the product desired and may include conditions and fabrics described above or those described or shown in one or more of: U.S. Pat. No. 5,510,002 to Hermans et al.; U.S. Pat. No. 4,529,480 of Trokhan; U.S. Pat. No. 4,102,737 of Morton and U.S. Pat. No. 3,994,771 to Morgan, Jr. et al., the disclosures of which are hereby incorporated by reference into this section.

After wet shaping, web, W, is transferred over vacuum roll 230 impingement air-dry system in the machine direction 35 as shown. The apparatus of FIG. 22 generally includes a pair of drilled hollow cylinders 232, 234, a vacuum roll 236 therebetween as well as a hood 238 equipped with nozzles and air returns. In connection with FIG. 22, it should be noted that transfer of a web, W, over an open draw needs to be stabilized at high speeds. Rather than use an impingement-air dryer, after-dryer section 150 of FIG. 22 may include instead of cylinders 232, 234 of a throughdrying unit as is well known in the art and described in U.S. Pat. No. 3,432,936 to Cole et al., the disclosure of which is incorporated herein by reference.

Yet another after-drying section is disclosed in U.S. Pat. No. 5,851,353 which may likewise be employed in a wet-creped process using the apparatus of FIG. 19.

Figure 23:
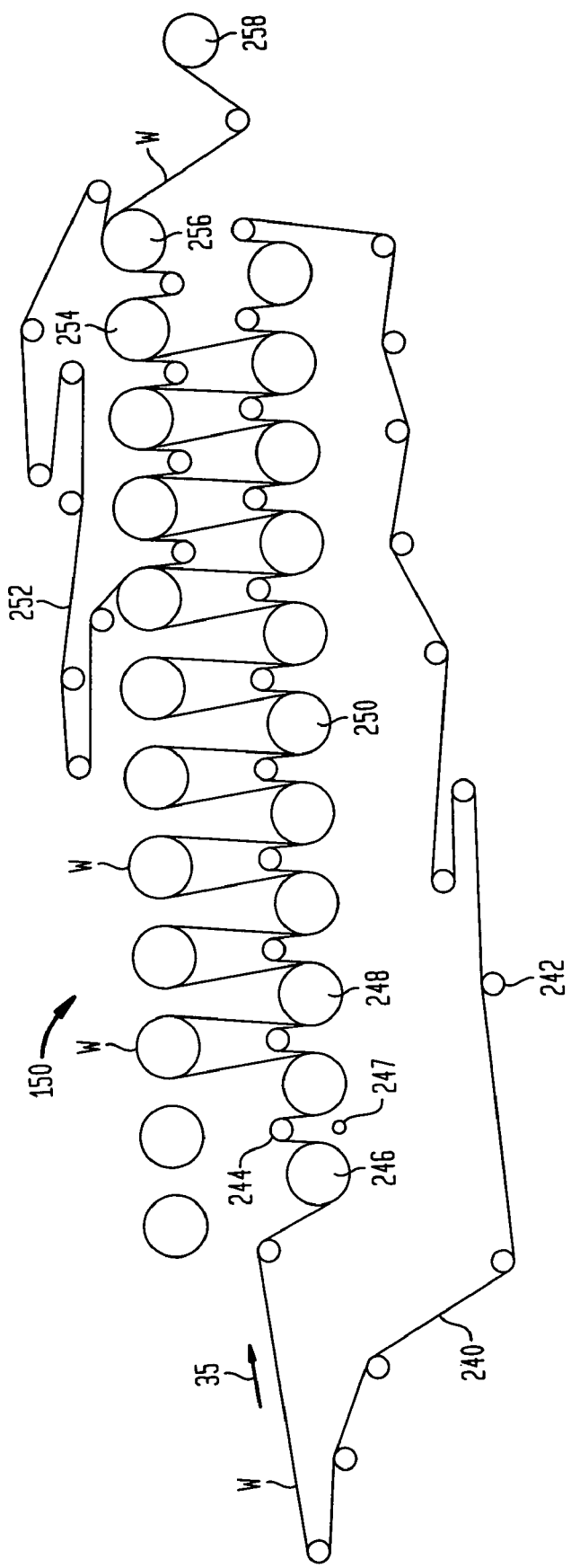
FIG. 23 is a diagram of another drying apparatus which may be used to dry a wet-creped web.

Still yet another after-drying section 150 is illustrated schematically in FIG. 23. After creping from the Yankee cylinder the web, W, is deposited on an after-dryer felt 240 which travels in machine direction 35 and forms an endless loop about a plurality of after-dryer felt rolls such as rolls 242, 244 and a plurality of after-dryer drums such as drums (sometimes referred to as cans) 246, 248 and 250.

A second felt 252 likewise forms an endless loop about a plurality of after-dryer drums and rollers as shown. The various drums are arranged in two rows and the web is dried as it travels over the drums of both rows and between rows as shown in the diagram. Felt 252 carries web, W, from drum 254 to drum 256, from which web, W, may be further processed or wound up on a take-up reel 258.

Figure 24:
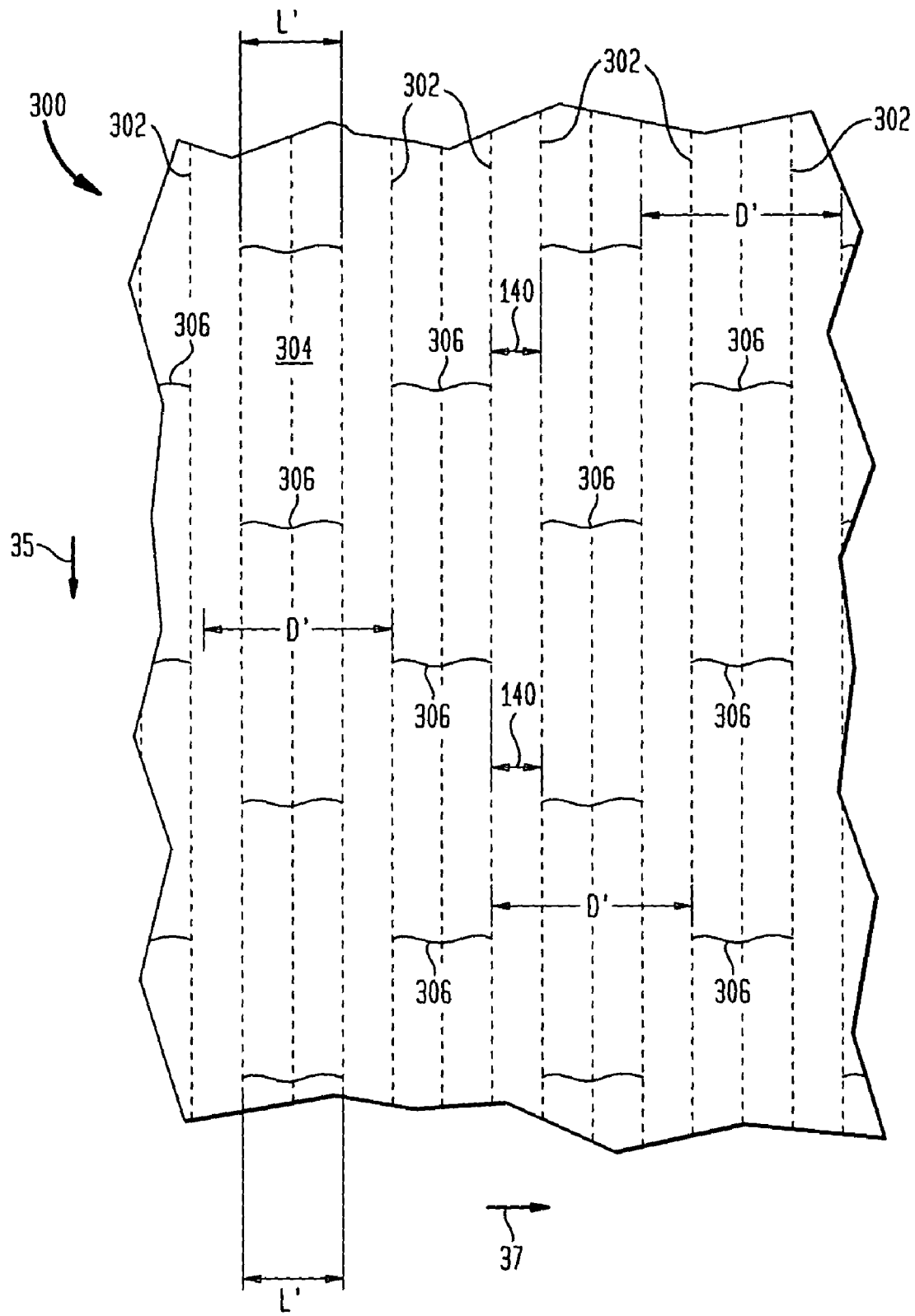
FIG. 24 is a schematic illustration of a portion of an embossed sheet of the invention.

Referring to FIG. 24, there is shown schematically a portion of an embossed sheet 300 with a plurality of ridges 302 extending in the machine direction 35 whose centerlines are indicated by the dashed lines, and wherein the center-to-center distance of adjacent ridges is indicated at 140. The frequency, F, of the ridges is the reciprocal of this distance; that is, ridges per inch. For example, if the distance between ridges is $1/12$", the frequency, F, is 12. The sheet has a surface 304 provided with a plurality of perforate embossments 306 which are formed by embossing rolls having CD oval elements configured generally as shown in FIGS. 3A–3D.

Embossments 306 extend in cross-machine direction 37 a distance, L', which is typically less than the cross direction length of the embossing elements at their base, depending on the angle of the outer edges of the embossing elements and the engagement of the rolls. Note that embossments 306 are spaced a lateral distance, D', which corresponds roughly to the lateral distance between embossing elements; however, the dimensions may be different depending upon the engagement and geometry of the elements. The distance, D', is also measured along CD 37 in cases where the embossments are offset.

While the invention has been illustrated in connection with numerous examples and embodiments, variations within the spirit and scope of the invention, set forth in the appended claims, will be readily apparent to those of skill in the art.

What is claimed is:

1. A method of embossing an absorbent web with an undulatory structure extending in the machine direction comprising:
    providing a web with a plurality of ridges extending in its machine direction to an embossing station;
        wherein the plurality of ridges extending in the machine direction of the web occur at a frequency, F, across the web; and
    embossing the web at the embossing station between a first and second embossing roll, at least one of which rolls is provided with a plurality of embossing elements and wherein the rolls are thereby configured to define therebetween a plurality of embossing nips;
        wherein at least a portion of the nips defined by the embossing rolls are substantially oriented in a cross-machine direction with respect to the web and have a cross direction length, L, wherein the product F×L is from about 0.1 to about 5.

2. The method according to claim 1, wherein the product F×L is from about 0.2 to about 3.

3. The method according to claim 2, wherein the product F×L is from about 0.3 to about 2.

4. The method according to claim 2, wherein the product F×L is from about 0.5 to about 1.5.

5. The method according to claim 1, wherein the product F×L is from about 1 to about 4.

6. A method of embossing an absorbent web with an undulatory structure extending in the machine direction comprising:
    providing a web with a plurality of ridges extending in its machine direction to an embossing station;
        wherein the plurality of ridges extending in the machine direction of the web occur at a frequency, F, across the web; and
    embossing the web at the embossing station between a first and second embossing roll, at least one of which rolls is provided with a plurality of embossing elements and wherein the rolls are thereby configured to define therebetween a plurality of embossing nips;

wherein at least a portion of the embossing nips defined by the embossing rolls are substantially oriented in the cross-machine direction with respect to the web, and comprise perforate embossing nips, which have a cross direction length, L, wherein the product F×L is from about 0.1 to about 5.

7. A method of embossing an absorbent web with an undulatory structure extending in the machine direction comprising:

providing a web with a plurality of ridges extending in its machine direction to an embossing station;

wherein the plurality of ridges extending in the machine direction of the web occur at a frequency, F, across the web; and embossing the web at the embossing station between a first and second embossing roll, at least one of which rolls is provided with a plurality of embossing elements and wherein the rolls are thereby configured to define therebetween a plurality of embossing nips;

wherein at least a portion of the nips defined by the embossing rolls are substantially oriented in a cross-machine direction with respect to the web and have a cross direction length, L, wherein the product F×L is from about 0.1 to about 5, and said cross-direction oriented embossing nips are defined by embossing elements on opposed embossing rolls and the embossing element engagement is at least about 15 mils.

8. The method according to claim 7, wherein the cross-direction oriented embossing nips are defined by embossing elements on opposed embossing rolls-and where the embossing element engagement is from about 16 to about 32 mils.

9. The method according to claim 7, wherein substantially all of the nips defined by the embossing rolls are substantially oriented in the cross direction.

10. The method according to claim 7, wherein at least a portion of the embossing elements are male elements that are substantially oval shaped.

11. The method according to claim 7, wherein at least a portion of the embossing elements are male elements that are substantially hexagonal shaped.

12. The method according to claim 7, wherein at least a portion of the embossing elements are male elements that are substantially rectangular shaped.

13. The method according to claim 7, wherein the cross-machine direction oriented nips defined by the embossing rolls are at an angle of from about 60° to about 120° from the machine direction.

14. The method according to claim 7, wherein the cross-machine direction oriented nips defined by the embossing rolls are at an angle of from about 85° to about 95° from the machine direction.

15. The method according to claim 7, wherein at least a portion of the embossing elements are male elements having a height of at least about 15 mils.

16. The method according to claim 7, wherein at least a portion of the embossing elements are male elements having a height of at least about 30 mils.

17. The method according to claim 7, wherein the cross-machine direction oriented nips are defined by embossing elements which are in full-step alignment.

18. The method according to claim 7, wherein the cross-machine direction oriented nips are defined by embossing elements which are in half-step alignment.

19. The method according to claim 7, wherein the cross-machine direction oriented nips are defined by embossing elements which are in quarter-step alignment.

20. The method according to claim 7, wherein the cross-machine direction oriented nips are defined by embossing elements which have angled sidewalls, wherein the sidewalls have an angle of less than about 20°.

21. The method according to claim 7, wherein the embossing nips oriented in the cross-machine direction comprise perforate embossing nips and the embossing step is operative to reduce the dry tensile ratio of the web.

22. The method according to claim 7, wherein the embossing nips comprise perforate embossing nips and the process of embossing the web is operative to reduce the wet tensile ratio of the web.

23. The method according to claim 7, wherein at least a portion of the embossing nips are perforate embossing nips and wherein the process of embossing the web is operative to increase the transluminance ratio of the web.

24. The method according to claim 7, operative to reduce the MD dry tensile strength of the web by less than about 15%.

25. The method according to claim 7, operative to reduce the MD dry tensile strength of the web by at least about 10%.

26. The method according to claim 7, operative to reduce the MD dry tensile strength of the web by from about 35% to about 65%.

27. The method according to claim 7, operative to reduce the CD dry tensile strength by less than about 30%.

28. The method according to claim 7, operative to reduce the CD dry tensile strength by less than about 25%.

29. The method according to claim 7, operative to reduce the CD dry tensile strength by less than about 20%.

30. The method according to claim 7, operative to reduce the CD dry tensile strength by less than about 15%.

31. The method according to claim 7, operative to impart a caliper gain of at least about 15%.

32. The method according to claim 30, operative to impart a caliper gain of at least about 20%.

33. The method according to claim 31, operative to impart a caliper gain of at least about 25%.

34. The method according to claim 32, operative to impart a caliper gain of at least about 30%.

35. The method according to claim 33, operative to impart a caliper gain of at least about 40%.

36. A method of embossing an absorbent web with an undulatory structure extending in the machine direction comprising:

providing a web with a plurality of ridges extending in its machine direction to an embossing station;

wherein the plurality of ridges extending in the machine direction of the web occur at a frequency, F, across the web; and embossing the web at the embossing station between a first and second embossing roll, at least one of which rolls is provided with a plurality of embossing elements, wherein at least a portion of the embossing elements have a height of at least about 30 mils, and wherein the rolls are thereby configured to define therebetween a plurality of embossing nips;

wherein at least a portion of the nips defined by the embossing rolls are substantially oriented in a cross-machine direction with respect to the web and have a cross direction length, L, wherein the product F×L is from about 0.1 to about 5, and wherein the cross-direction oriented embossing nips are defined by embossing elements on opposed embossing rolls and where the engagement of opposed elements is at least about 15 mils.

37. The method according to claim 36, wherein at least a portion of the embossing elements have a height of at least about 30 mils wherein the cross-direction oriented embossing nips are defined by embossing elements on opposed embossing rolls and where the engagement of opposed elements is at least about 24 mils.

38. A method of embossing an absorbent web with an undulatory structure extending in the machine direction comprising:
    providing a web with a plurality of ridges extending in its machine direction to an embossing station, wherein the web is a creped web prepared with an undulatory creping blade, having a biaxially undulatory structure with crepe bars extending in the cross direction and ridges extending in the machine direction;
        wherein the plurality of ridges extending in the machine direction of the web occur at a frequency, F, across the web; and
    embossing the web at the embossing station between a first and second embossing roll, at least one of which rolls is provided with a plurality of embossing elements and wherein the rolls are thereby configured to define therebetween a plurality of embossing nips;
        wherein at least a portion of the nips defined by the embossing rolls are substantially oriented in a cross-machine direction with respect to the web and have a cross direction length, L, wherein the product F×L is from about 0.1 to about 5.

39. The method according to claim 38, wherein the web has from about 4 to about 50 ridges per inch extending in the machine direction.

40. The method according to claim 39, wherein the web has from about 8 to about 25 ridges per inch extending in the machine direction.

41. The method according to claim 40, wherein the web has from about 10 to about 16 ridges per inch extending in the machine direction.

42. The method according to claim 38, wherein the web has from about 4 to about 50 ridges per inch extending in the machine direction and from about 10 to about 150 crepe bars per inch extending in the cross-machine direction of the web.

43. A method of embossing an absorbent web with an undulatory structure extending in the machine direction comprising:
    providing a web with a plurality of ridges extending in its machine direction to an embossing station;
        wherein the plurality of ridges extending the machine direction of the web occur at a frequency, F, across the web; and
    embossing the web at the embossing station between a first and second embossing roll, at least one of which rolls is provided with a plurality of embossing elements and the rolls are thereby configured to define therebetween a plurality of embossing nips,
        wherein at least a portion of the nips defined by the embossing rolls are the embossing rolls are substantially oriented in a cross-machine direction with respect to the web, having a cross direction length, L, and are laterally spaced at a distance, D, with the proviso that:
            (a) the product F×L is between about 0.1 and about 5 or (b) the product F×D is between about 0.1 and about 5.

44. The method according to claim 43, wherein the product F×L is from about 0.2 to about 3.

45. The method according to claim 43, wherein the product F×D is from about 0.2 to about 3.

46. The method according to claim 43, wherein (a) product F×L is from about 1 to about 4; or (b) the product F×D is from about 1 to about 4.

47. A method of embossing an absorbent web with an undulatory structure extending in the machine direction comprising:
    providing a web with a plurality of ridges extending in its machine direction to an embossing station;
        wherein the plurality of ridges extending the machine direction of the web occur at a frequency, F, across the web; and
    embossing the web at the embossing station between a first and second embossing roll, at least one of which rolls is provided with a plurality of embossing elements and the rolls are thereby configured to define therebetween a plurality of embossing nips,
        wherein at least a portion of the embossing nips defined by the embossing rolls are substantially oriented in the cross-machine direction with respect to the web, and comprise perforate embossing nips, which have a cross direction length, L, and are laterally spaced at a distance, D, with the proviso that: (a) the product F×L is between about 0.1 and about 5 or (b) the product F×D is between about 0.1 and about 5.

48. The method according to claim 47, wherein substantially all of the nips defined by the embossing rolls are substantially oriented in the cross-machine direction.

49. The method according to claim 47, wherein at least a portion of the embossing elements are male elements that are substantially oval shaped.

50. The method according to claim 47, wherein the process of embossing the web is operative to reduce the dry tensile ratio of the web.

51. The method according to claim 47, wherein the process of embossing the web is operative to reduce the wet tensile ratio of the web.

52. The method according to claim 47, the process of embossing the web is operative to increase the transluminance ratio of the web.

53. A method of embossing an absorbent web with an undulatory structure extending in the machine direction comprising:
    providing a web with a plurality of ridges extending in its machine direction to an embossing station, wherein the web is a creped web prepared with an undulatory creping blade, having a biaxially undulatory structure with crepe bars extending in the cross-machine direction and ridges extending in the machine direction;
        wherein the plurality of ridges extending the machine direction of the web occur at a frequency, F, across the web; and
    embossing the web at the embossing station between a first and second embossing roll, at least one of which rolls is provided with a plurality of embossing elements and the rolls are thereby configured to define therebetween a plurality of embossing nips,
        wherein at least a portion of the nips defined by the embossing rolls are the embossing rolls are substantially oriented in a cross-machine direction with respect to the web, having a cross direction length, L, and are laterally spaced at a distance, D, with the proviso that:
(a) the product F×L is between about 0.1 and about 5
or (b) the product F×D is between about 0.1 and about 5.

54. The method according to claim 53, wherein the web has from about 4 to about 50 ridges per inch extending in the machine direction.

55. The method according to claim 54, wherein the web has from about 8 to about 25 ridges per inch extending in the machine direction.

56. The method according to claim 55, wherein the web has from about 10 to about 16 ridges per inch extending in the machine direction.

57. The method according to claim 53, wherein the web has from about 4 to about 50 ridges per inch extending in the machine direction and from about 10 to about 150 crepe bars per inch extending in the cross-machine direction.

* * * * *

UNITED STATES PATENT AND TRADEMARK OFFICE
CERTIFICATE OF CORRECTION

PATENT NO. : 7,037,406 B2  
APPLICATION NO. : 10/635663  
DATED : May 2, 2006  
INVENTOR(S) : Thomas N. Kershaw et al.

Page 1 of 1

It is certified that error appears in the above-identified patent and that said Letters Patent is hereby corrected as shown below:

In Col. 4, line 41, insert --in-- after "extending";  
In Col. 5, line 26, change "BRIEF DESCRIPTION OF THE INVENTION" to --BRIEF DESCRIPTION OF THE DRAWINGS--;  
In Col. 6, line 44, delete "are";  
In Col. 9, line 6, delete "20";  
In Col. 10, line 16, delete "directions element" and insert --direction elements--;  
In Col. 10, line 55, change "on" to --an--;  
In Col. 13, line 32, change "00.005599" to --0.005599--;  
In Col. 18, line 57, change "RESILENCY" to --RESILIENCY--;  
In Cols. 21 and 22, Table 5, change "FP*" to --FP--;  
In Col. 29, line 28, chaneg "114" to --118--;  
In Col. 31, line 35, change "holder" to --"holder--;  
In Col. 32, line 38, change "bout" to --about--;  
In Col. 33, line 50, delete "of";  
In Col. 36, line 41 (Claim 32), change "30" to --31--;  
In Col. 36, line 43 (Claim 32), change "31" to --32--;  
In Col. 36, line 45 (Claim 33), change "32" to --33--; and  
In Col. 36, line 47 (Claim 34), change "33" to --34--.

Signed and Sealed this

Twenty-eighth Day of November, 2006

JON W. DUDAS  
*Director of the United States Patent and Trademark Office*